(12) United States Patent
Xu et al.

(10) Patent No.: US 7,675,667 B2
(45) Date of Patent: Mar. 9, 2010

(54) ELECTROPOLYMERIZATION OF ENHANCED ELECTROCHROMIC (EC) POLYMER FILM

(75) Inventors: Chunye Xu, Seattle, WA (US); Lu Liu, Seattle, WA (US); Minoru Taya, Mercer Island, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/253,110

(22) Filed: Oct. 16, 2008

(65) Prior Publication Data

US 2009/0052002 A1 Feb. 26, 2009

Related U.S. Application Data

(60) Division of application No. 10/917,954, filed on Aug. 13, 2004, now Pat. No. 7,450,290, and a continuation-in-part of application No. 10/755,433, filed on Jan. 12, 2004, now Pat. No. 7,002,722, which is a division of application No. 10/180,222, filed on Jun. 25, 2002, now Pat. No. 6,747,780.

(60) Provisional application No. 60/523,007, filed on Nov. 18, 2003, provisional application No. 60/495,310, filed on Aug. 14, 2003, provisional application No. 60/364,418, filed on Mar. 14, 2002, provisional application No. 60/324,205, filed on Sep. 21, 2001, provisional application No. 60/300,675, filed on Jun. 25, 2001.

(51) Int. Cl.
*G02F 1/15* (2006.01)

(52) U.S. Cl. .................. 359/265; 359/273; 359/275

(58) Field of Classification Search ................ 359/265, 359/273
See application file for complete search history.

(56) References Cited

U.S. PATENT DOCUMENTS

| | | | | |
|---|---|---|---|---|
| 4,702,963 | A | 10/1987 | Phillips et al. | 428/426 |
| 4,761,061 | A | 8/1988 | Nishiyama et al. | 359/265 |
| 5,124,833 | A | 6/1992 | Barton et al. | 359/269 |
| 5,471,339 | A * | 11/1995 | Ise et al. | 359/275 |
| 5,598,293 | A | 1/1997 | Green | 359/275 |
| 5,910,854 | A * | 6/1999 | Varaprasad et al. | 359/273 |
| 6,373,618 | B1 * | 4/2002 | Agrawal et al. | 359/265 |
| 6,667,825 | B2 * | 12/2003 | Lu et al. | 359/265 |
| 6,950,220 | B2 | 9/2005 | Abramson et al. | 359/265 |
| 2005/0025980 | A1 | 2/2005 | Agrawal et al. | 428/426 |
| 2007/0292606 | A1 | 12/2007 | Demiryont et al. | 427/126.5 |
| 2008/0203910 | A1 | 8/2008 | Reynolds | 313/506 |

FOREIGN PATENT DOCUMENTS

JP 62265630 11/1987

* cited by examiner

*Primary Examiner*—Jessica T Stultz
(74) *Attorney, Agent, or Firm*—Ronald M. Anderson

(57) ABSTRACT

Devices including EC monomers polymerized using chronoamperometry to deposit a very thin homogeneous layer followed by cyclic voltammetry to increase the density of the EC polymer film. Another aspect of the present invention is directed to specific web like configurations for a grid of conductive material deposited onto a transparent substrate. The web like configuration is based either on concentric circles, or on concentric ellipses. Yet another aspect of the present invention is directed to an imaging system including a digital window that is disposed between a prism and a patterned analytic layer.

16 Claims, 23 Drawing Sheets

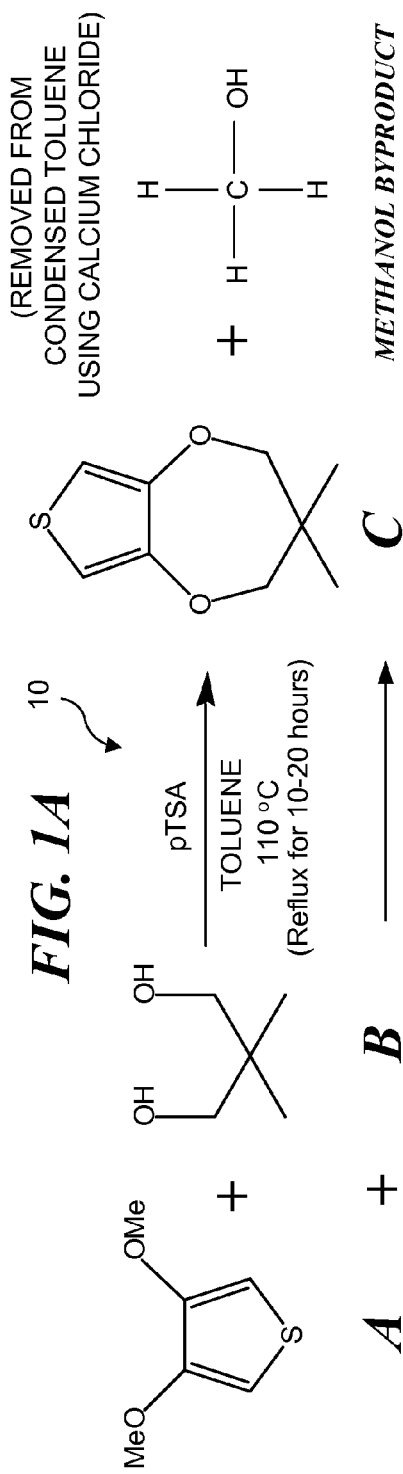
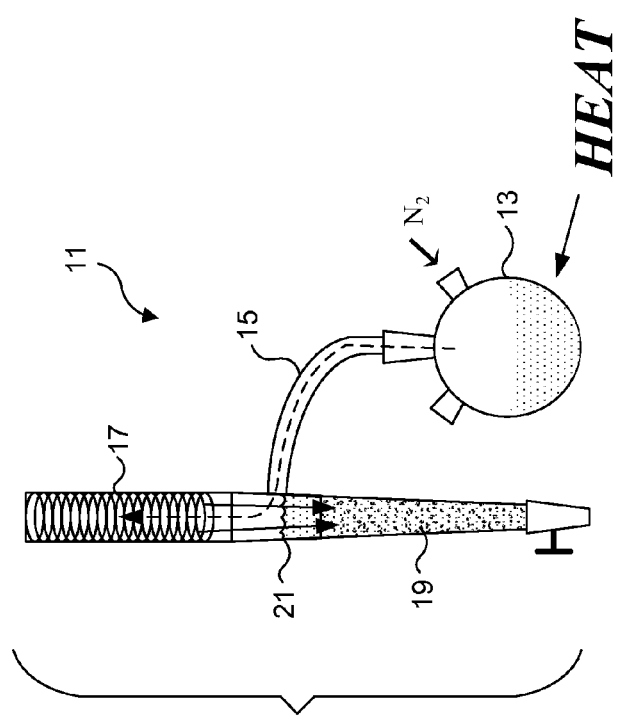
FIG. 1A
FIG. 1B

CATHODIC EC POLYMER: PPRODOT-ME$_2$:
POLY[3,3- DIMETHYLE -3,4- DIHYDRO -2H-THIENO [3,4-B][1,4] DIOXEPINE]

ANODIC EC POLYMER: PBEODOT-NCH$_3$Cz:
POLY[3,6-BIS(2-(3,4-ETHYLENEDIOXYTHIOPHENE))-N-METHYLCARBAZOLE

*TRANSPARENT/OXIDIZED STATE*
*NO VOLTAGE APPLIED (OR POSITIVE VOLTAGE APPLIED)*

*COLORED/REDUCED STATE*
*VOLTAGE APPLIED (NEGATIVE VOLTAGE APPLIED)*

CATHODIC EC POLYMER: PPRODOT-ME$_2$

POLY[3,3- DIMETHYLE -3,4- DIHYDRO -2H-THIENO [3,4-B][1,4] DIOXEPINE]

COUNTERELECTRODE = GOLD OR CONDUCTIVE CARBON PATTERNED ON TRANSPARENT SUBSTRATE

TRANSPARENT/OXIDIZED STATE
NO VOLTAGE APPLIED (OR POSITIVE VOLTAGE APPLIED)

COLORED/REDUCED STATE
VOLTAGE APPLIED (NEGATIVE VOLTAGE APPLIED)

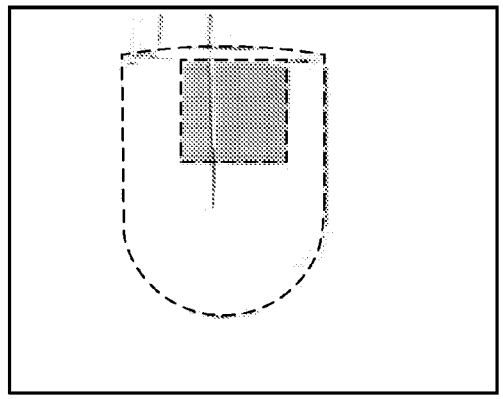
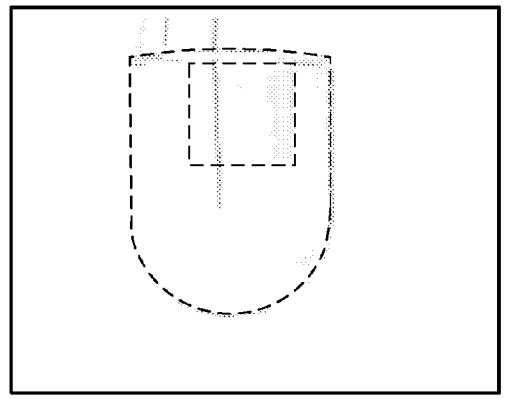
*FIG. 26A*  *FIG. 26B*
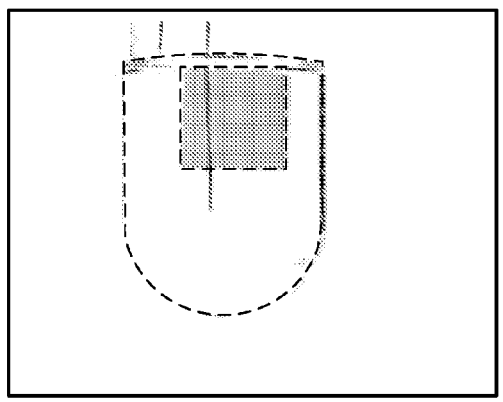
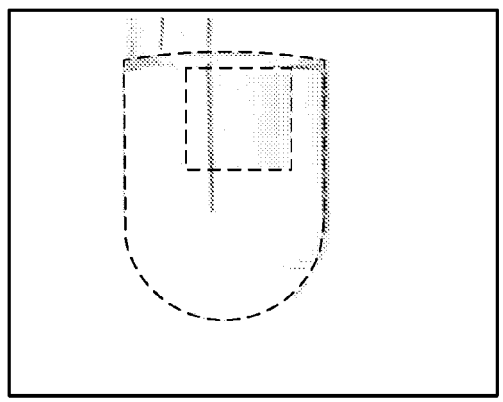
*FIG. 27A*  *FIG. 27B*

ELECTROPOLYMERIZATION OF ENHANCED ELECTROCHROMIC (EC) POLYMER FILM

RELATED APPLICATIONS

This application is a divisional application based on prior copending patent application Ser. No. 10/917,954, filed on Aug. 13, 2004, which itself is based on two prior provisional applications, Ser. No. 60/495,310, filed on Aug. 14, 2003, and Ser. No. 60/523,007, filed on Nov. 18, 2003, the benefits of the filing dates of which are hereby claimed under 35 U.S.C. §120 and 35 U.S.C. §119(e). Prior copending patent application Ser. No. 10/917,954 is also a continuation-in-part of prior patent application Ser. No. 10/755,433, filed on Jan. 12, 2004, which issued as U.S. Pat. No. 7,002,722 on Feb. 21, 2006, and which itself is a divisional of prior U.S. patent application Ser. No. 10/180,222, filed on Jun. 25, 2002, which issued as U.S. Pat. No. 6,747,780 on Jun. 8, 2004, and which itself is based on three prior provisional applications, including Ser. No. 60/300,675, filed on Jun. 25, 2001, Ser. No. 60/324,205, filed on Sep. 21, 2001, and Ser. No. 60/364,418, filed on Mar. 14, 2002, the benefits of the filing dates of which are hereby claimed under 35 U.S.C. §120 and §119(e).

BACKGROUND

Electrochromic (EC) materials are a subset of the family of chromogenic materials, which includes photochromic materials, and thermochromic materials. These are materials that change their tinting level or opacity when exposed to light photochromic), heat (thermochromic) or electricity (electrochromic). Chromogenic materials have attracted widespread interest in applications relating to the transmission of light.

An early application for chromogenic materials was in sunglasses or prescription eyeglasses that darken when exposed to the sun. Such photochromic materials were first developed by researchers at Corning Incorporated in the late 1960s. Since that time, it has been recognized that chromogenic materials could potentially be used to produce window glass that can vary the amount of light transmitted, although the use of such materials is clearly not limited to that prospective application. Indeed, EC technology is already employed in the displays of digital watches.

Several different distinct types of EC materials are known. The primary three types are inorganic thin films, organic polymer films, and organic solutions. For many applications, the use of a liquid material is inconvenient, and as a result, inorganic thin films and organic polymer films appear to be more industrially applicable.

For inorganic thin film based EC devices, the EC layer is typically tungsten oxide ($WO_3$). U.S. Pat. Nos. 5,598,293; 6,005,705; and 6,136,161 describe an inorganic thin film EC device based on a tungsten oxide EC layer. Other inorganic EC materials, such as molybdenum oxide, are also known. While many inorganic materials have been used as EC materials, difficulties in processing and slow response time associated with many inorganic EC materials have created the need for different types of EC materials.

Conjugated, redox-active polymers represent one different type of EC material. These polymers (cathodic or anodic polymers) are inherently electrochromic and can be switched electrochemically or chemically between different color states. A family of redox-active copolymers are described in U.S. Pat. No. 5,883,220. Another family of nitrogen based heterocyclic organic EC materials is described in U.S. Pat. No. 6,197,923. Research into still other types of organic film EC materials continues, in hopes of identifying or developing EC materials that will be useful in EC windows. There still exists room for improvement and development of new types of EC organic polymer films, and methods of making EC organic polymer films. For example, it would be desirable to develop EC organic polymer films and methods for making the same that provide certain desirable properties, such as specific colors, long-term stability, rapid redox switching, and large changes in opacity with changes of state.

To make an EC device that exhibits different opacities in response to a voltage, a multilayer assembly is required. In general, the two outside layers of the assembly are transparent electronic conductors. Within the outside layers is a counter-electrode layer and an EC layer, between which is disposed an ion conductor layer. When a low voltage is applied across the outer conductors, ions moving from the counter-electrode to the EC layer cause the assembly to change color. Reversing the voltage moves ions from the EC layer back to the counter-electrode layer, restoring the device to its previous state. Of course, all of the layers are preferably transparent to visible light. While some configurations of counter-electrodes are known, it would be desirable to provide additional counter-electrode configurations, to facilitate the development of new and improved EC devices.

While EC windows, or smart windows as they are sometimes called, are expected to represent a significant commercial application of EC technology, one additional potential use of an EC is in producing displays, sometimes referred to as smart displays, or digital windows (DWs). One promising application for DW systems relates to deoxyribonucleic acid (DNA) chip reading. Prior art DNA chip reading technology has relied on the use of custom photo masks. It would be desirable to provide DW based alternatives.

SUMMARY

A first aspect of the present invention is directed to specific configurations for a grid of conductive material deposited onto a transparent substrate. The resulting grid and substrate are useful as a counter electrode in an EC polymer based device. A preferred substrate is substantially optically transparent. Glass and optically clear plastics are exemplary of preferred substrates.

A first embodiment of a counter-electrode useful for EC devices can be produced by placing a thin layer of conductive material on an optically transparent substrate in a web shaped grid pattern based on concentric circles. A grid pattern is employed because conductive materials are generally not transparent. If a film of conductive material were placed on the entire surface of a substrate, the resulting counter-electrode would likely exhibit a relatively low optical transmissivity, and could even be substantially opaque. An opaque counter-electrode is not desirable for use in many EC devices, where optical transmissivity is desired in at least one state. By using a grid pattern of conductive material deposited on a substrate, a counter-electrode that has better optical transmissivity can be achieved, because the conductive material does not cover the entire surface of the substrate. Generally, the more dense the grid, the lower the optical transmissivity of the counter-electrode. Useful conductors include gold and carbon.

A second embodiment of a counter-electrode useful for EC devices can be produced by placing a thin layer of conductive material on an optically transparent substrate in a web-shaped grid pattern based on concentric ellipses. Again, useful conductors include gold and carbon, and preferred substrates include optically transparent glass and plastic.

In each embodiment, the thickness of the substrate is preferably on the order of 0.7 mm, with the conductive layer being no thicker, and preferably, substantially thinner. A layer of titanium-tungsten (TiW) may be added to the glass substrate first to enhance the bonding of the gold to the substrate, while if carbon is employed as the conductor, such a layer is not required. Preferably, less than 25 percent of the substrate surface is covered with the conductive layer.

A second aspect of the present invention is directed to an imaging system including a DW for DNA chip and unknown molecules reading technology based on SPR imaging with high lateral resolution. Currently, DNA chip reading/writing technology requires expensive custom photo masks used in the photosynthesizing of oligonucleotides in DNA array fabrication. In this aspect of the present invention, a DW including a plurality of individually addressable pixels arranged in a grid format is employed in the place of the conventional photo mask. A voltage can be applied to each pixel individually, enabling selective masking to be achieved. At least one embodiment of this aspect of the present invention includes a flow cell, a patterned analytic layer, a light source directing light to the analytic layer along a first path, and a first optical element in the first path that polarizes the light. This embodiment includes a prism disposed in the first light path between the first optical element and the analytic layer, such that light traveling along the first path passes through the prism. A digital window is disposed between the prism and the analytic layer, such that the digital window can selectively control whether light from the light source traveling along the first path reaches the analytic layer first path, without effecting the transmission of light from the light source through the prism. The digital window includes a plurality of individually addressable pixels arranged in a grid format, each pixel being switchable between a transparent state and a non-transparent state by applying a voltage thereto. Each pixel preferably includes a laminated electrochromic structure having a cathodic electrochromic polymer layer. A plurality of electrical conductors are coupled to each pixel, such that a voltage can be individually selectively applied to each pixel. A power supply is electrically coupled to the electrical conductors and the light source. A second optical element is disposed along a second path. The second optical element focuses light traveling from the analytic surface and passes the light that is focused through the prism. A detector is disposed in the second path, to receive light focused by the second optical element.

A third aspect of the present invention is directed to devices including high quality EC polymer films. In a first embodiment, these high quality EC polymer films are formed using cyclic voltammetry to polymerize the EC monomer and to deposit the resultant polymer as a film on a substrate. Oxidative electrochemical polymerization of the monomer is preferably carried out using multiple scan cyclic voltammetry. Particularly preferred parameters include a voltage of +0.8 to ~–1.0 V, a scanning rate of 20 mV/s, and 10 cycles. The monomer is preferably dissolved into a solution 0.1 M of tetrobutylammonium perchlorate in propylene carbonate. The monomer is preferably present in a concentration of 0.01 M. A platinum wire can be used as the counter electrode. In a second embodiment, these high quality EC polymer films are formed using both cyclic voltammetry and chronoamperometry. EC monomers are prepared or obtained. A selected monomer is polymerized first using chronoamperometry, followed by cyclic voltammetry. Preferred parameters for chronoamperometry include the application of 0.88 V for 100 seconds, again using a platinum counter electrode, and a propylene carbonate solution with tetrobutylammonium perchlorate salt (0.01 M of the monomer and 0.1 M of tetrobutylammonium perchlorate). A very thin, very uniform layer of EC polymer is deposited onto a substrate using chronoamperometry. Then, multiple scan cyclic voltammetry is employed to deposit additional polymer onto the uniform layer deposited using chronoamperometry, until a dense polymer film is achieved. Preferred parameters for the cyclic voltammetry include a voltage range of +0.8 to ~–1.0 V, a scanning rate of about 20 mV/s and 10 cycles.

This application specifically incorporates by reference the disclosures and drawings of each patent application and issued patent identified above as a related application.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A is a schematic illustration of the synthesis of the monomer ProDOT-Me$_2$, which when polymerized may be beneficially employed as a cathodic EC polymer;

FIG. 1B is a schematic illustration of apparatus used in the synthesis of FIG. 1A;

Figure 2:
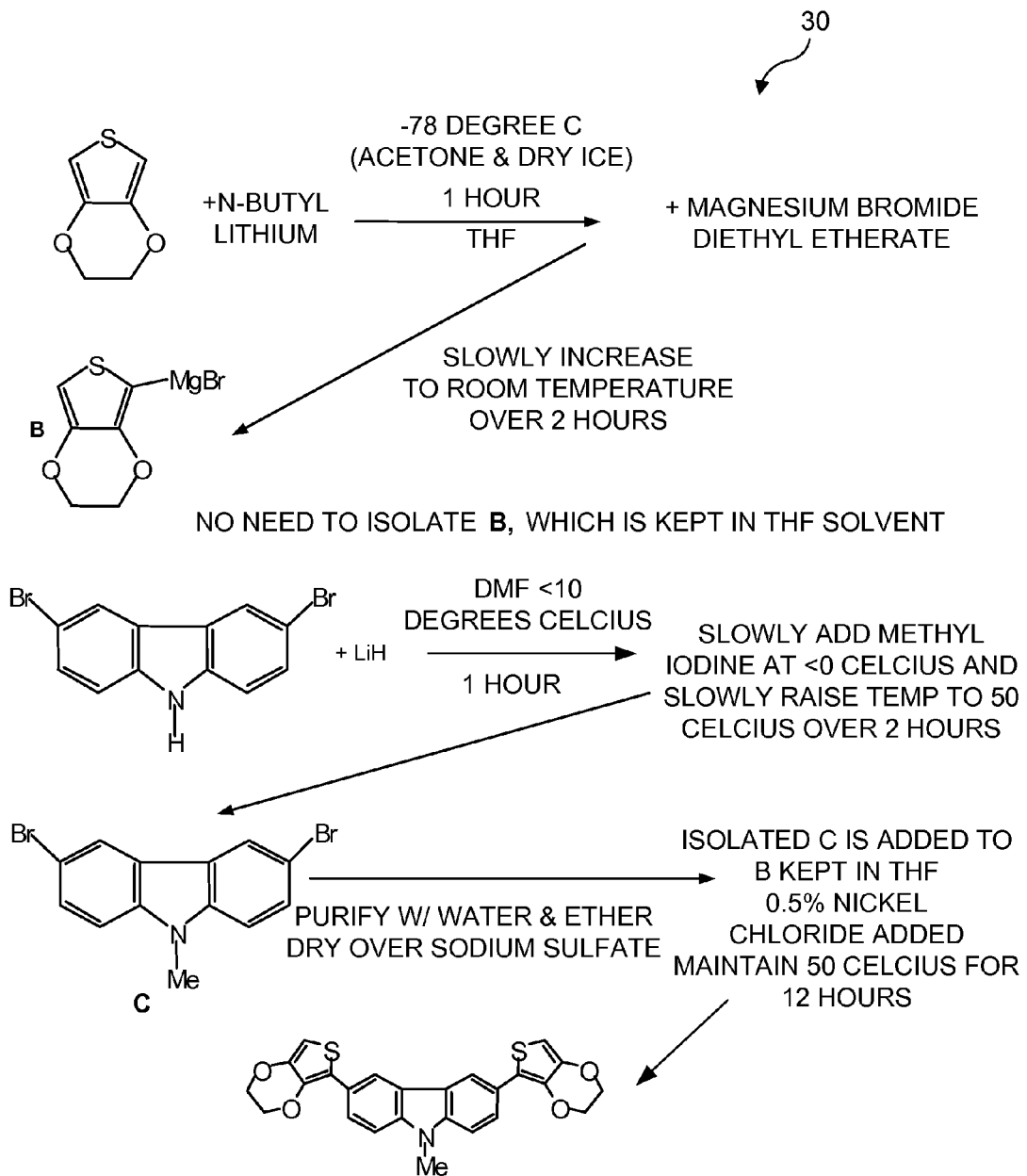
Figure 3A:
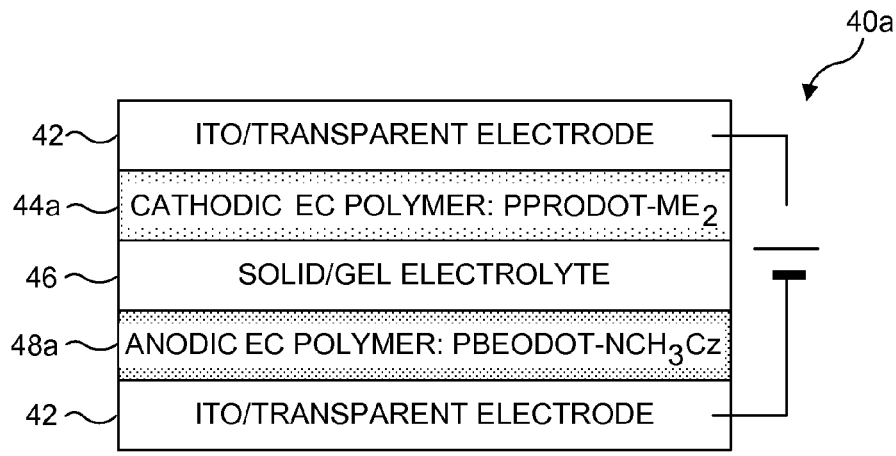
Figure 3B:
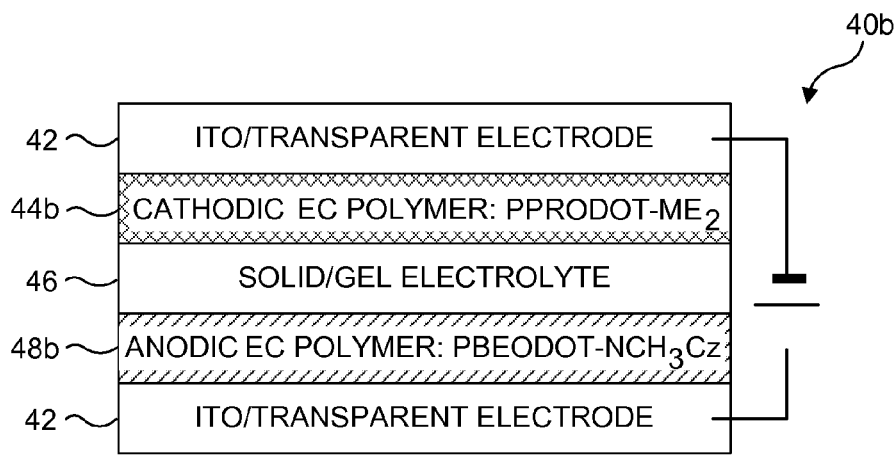
Figure 4A:
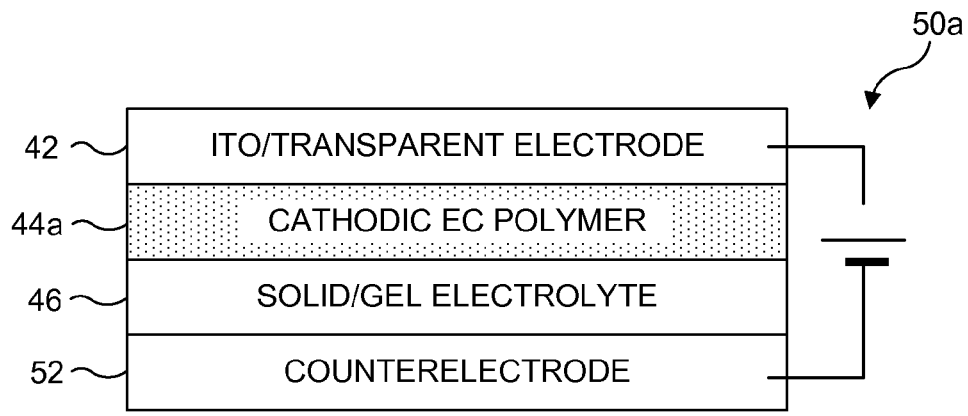
Figure 4B:
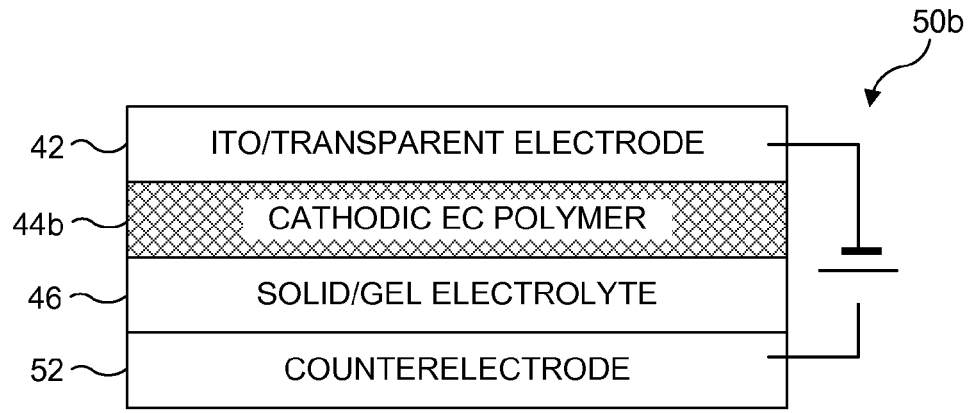
Figure 5A:
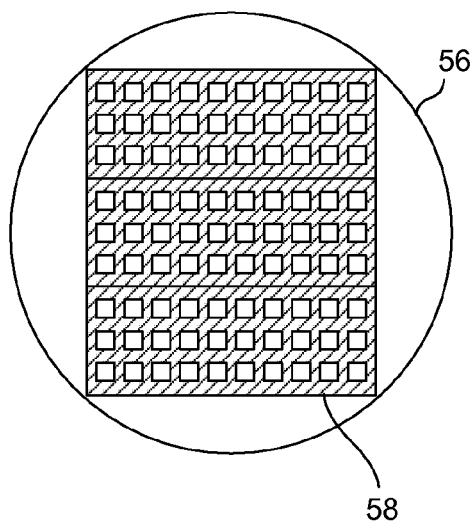
Figure 5B:
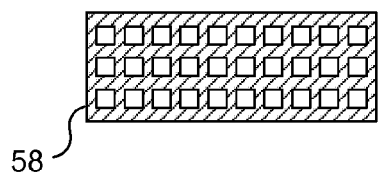
Figure 5C:
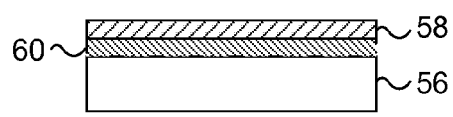
Figure 6A:
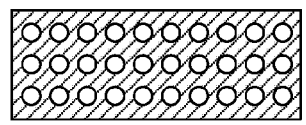
Figure 6B:
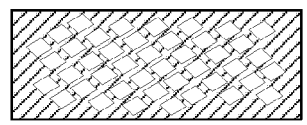
Figure 6C:
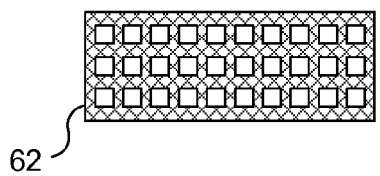
Figure 6D:
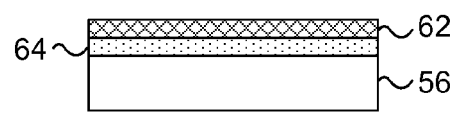
Figure 7A:
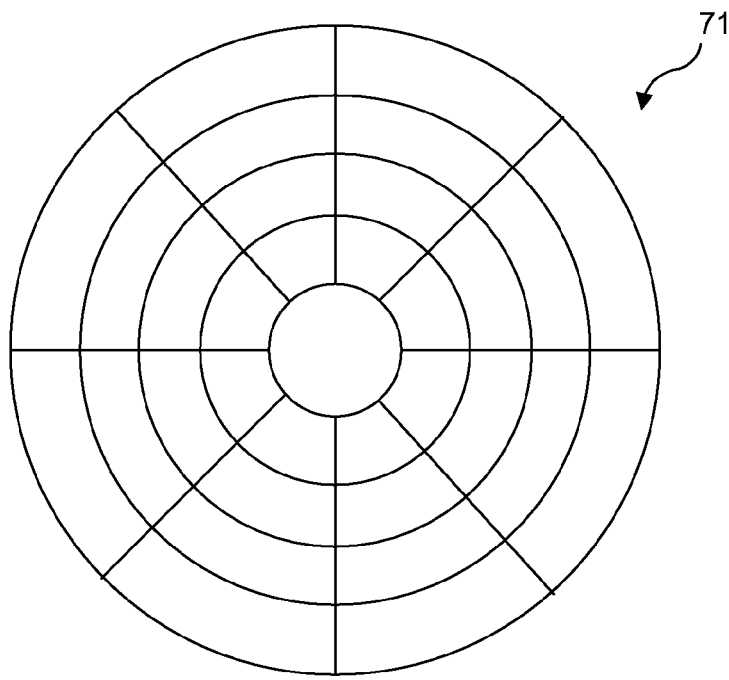
Figure 7B:
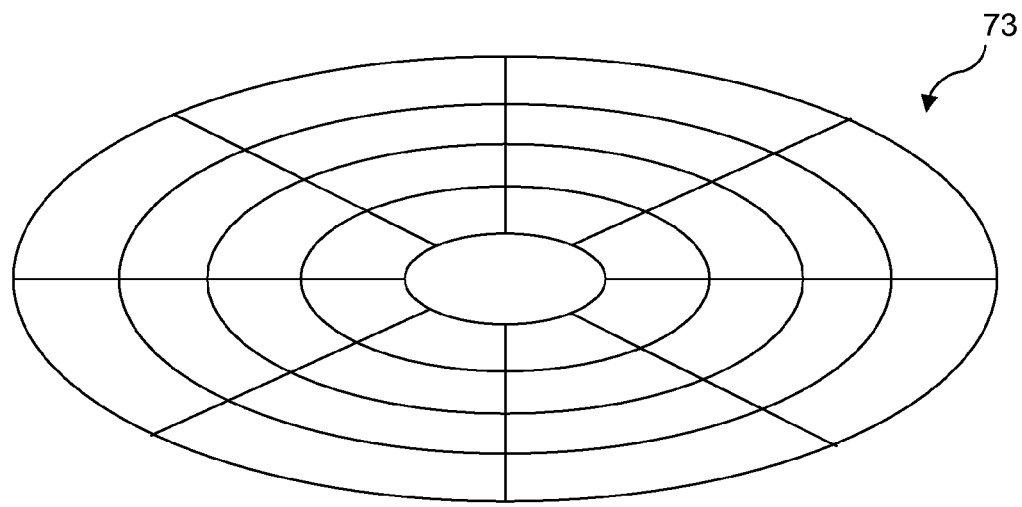
Figure 8A:
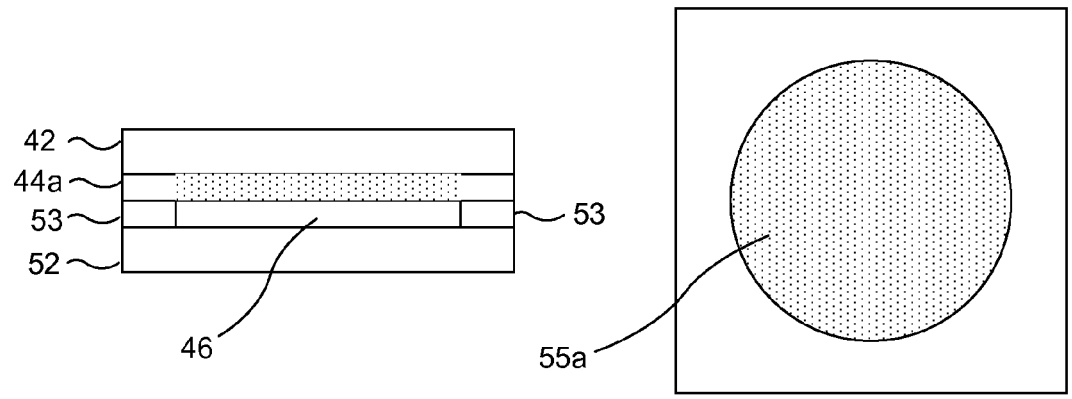
Figure 8B:
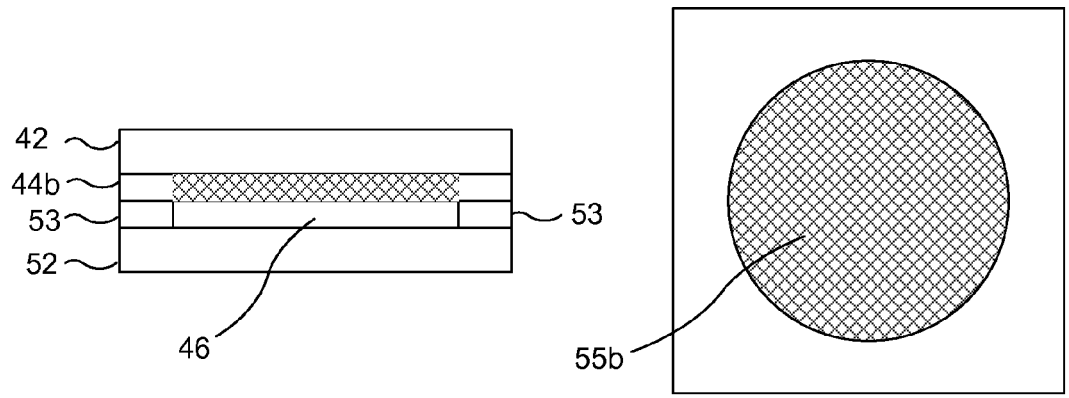
Figure 9A:
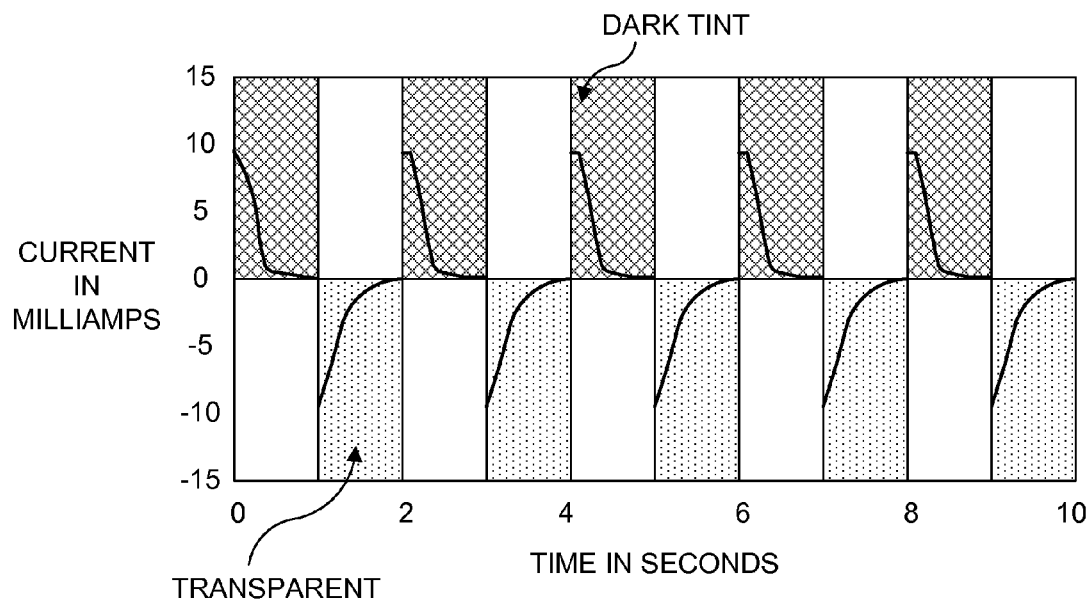
Figure 9B:
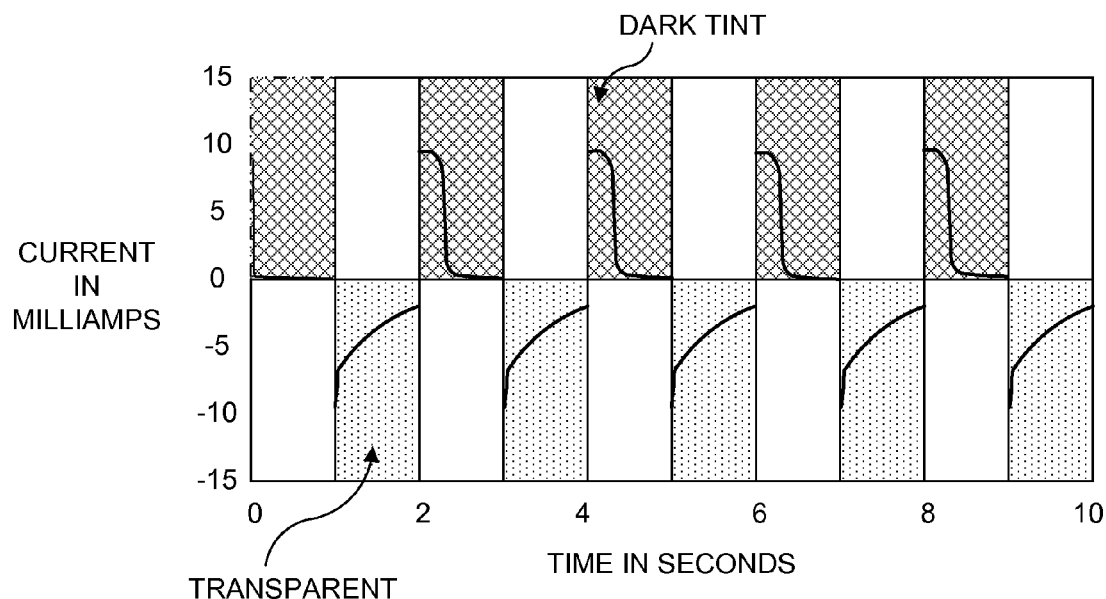
Figure 10A:
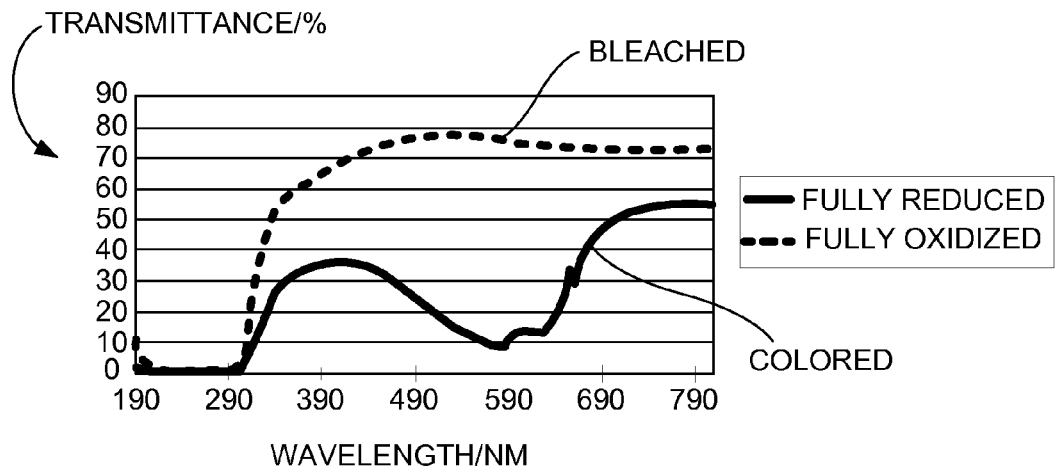
Figure 10B:
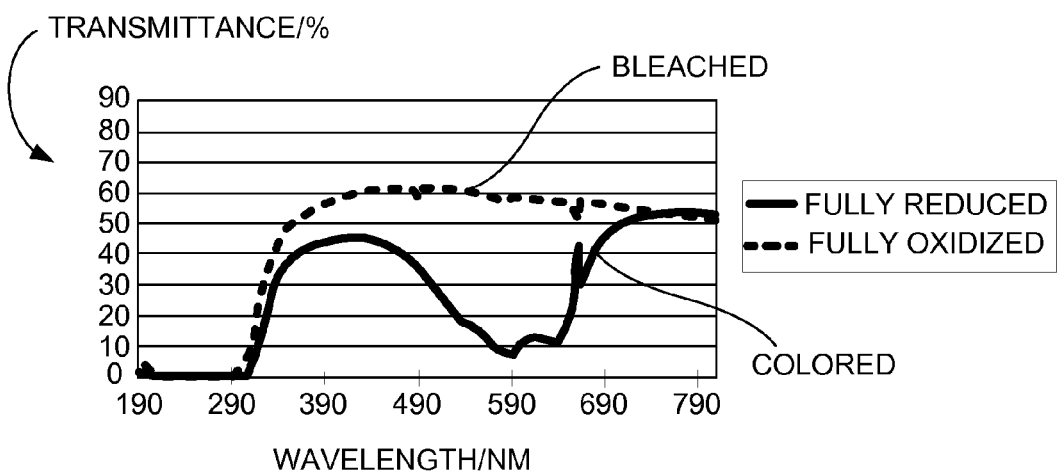
Figure 11A:
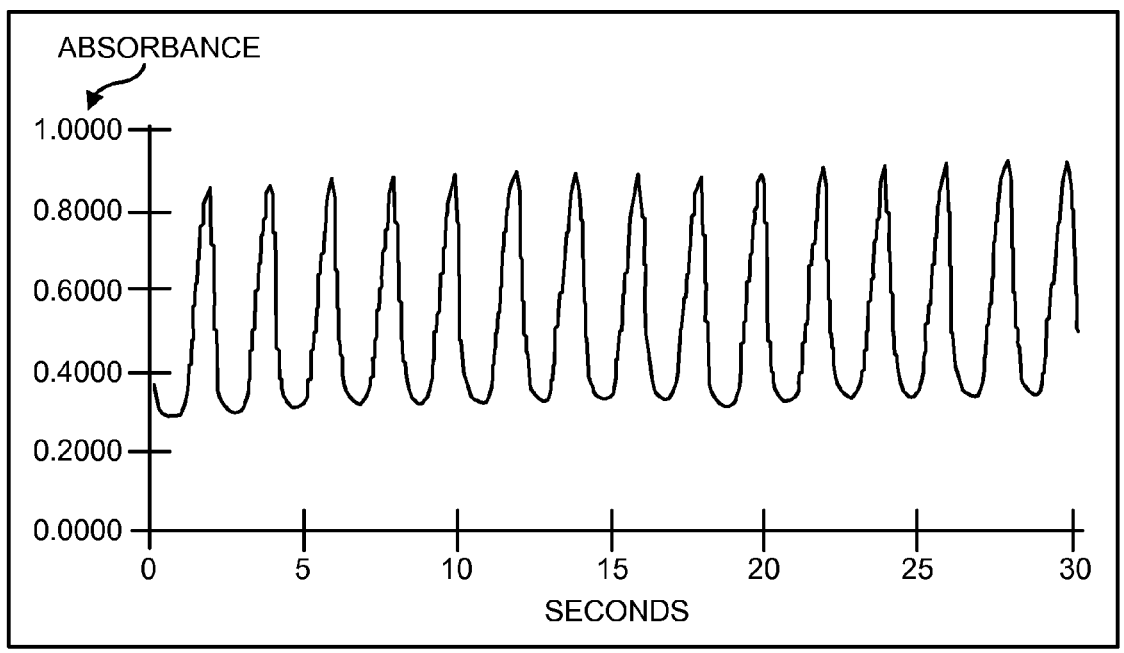
Figure 11B:
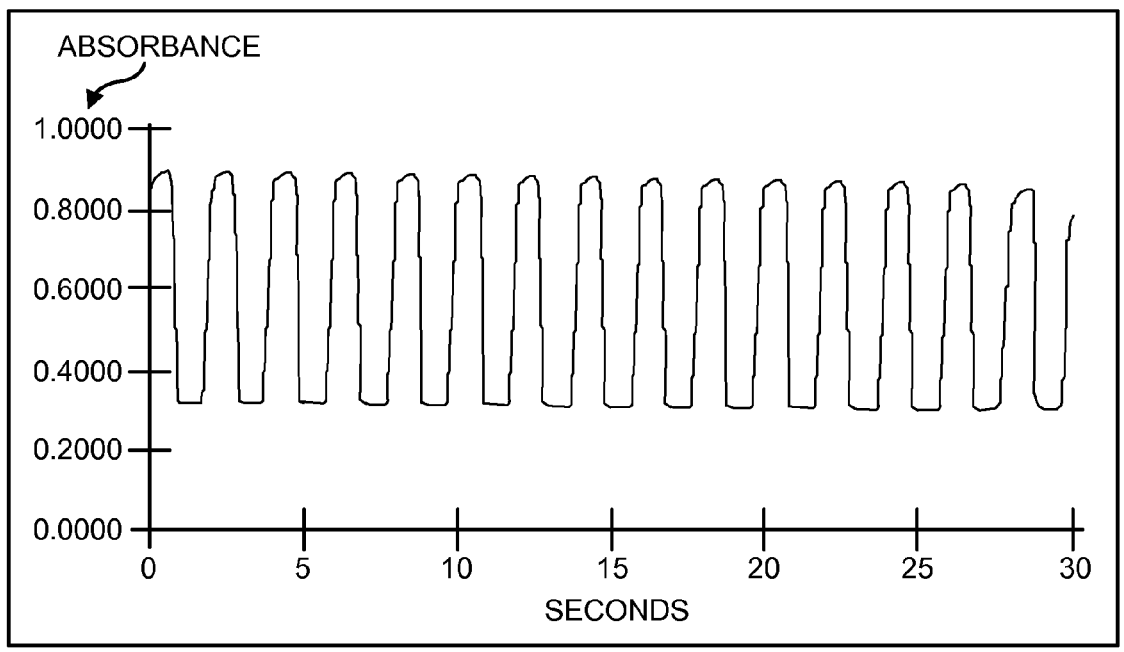
Figure 12:
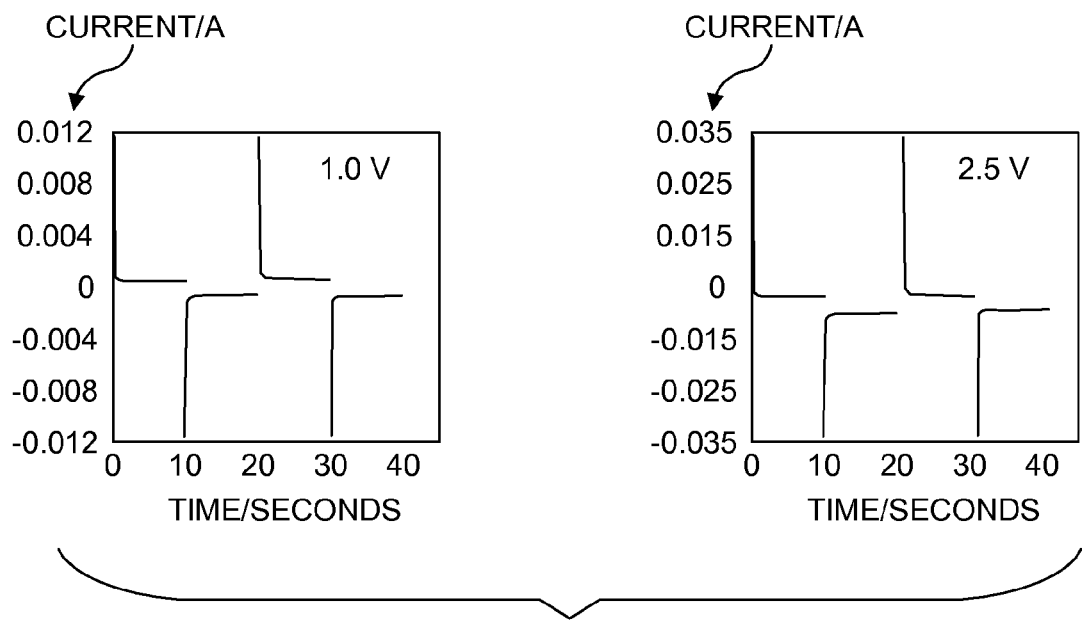
Figure 13:
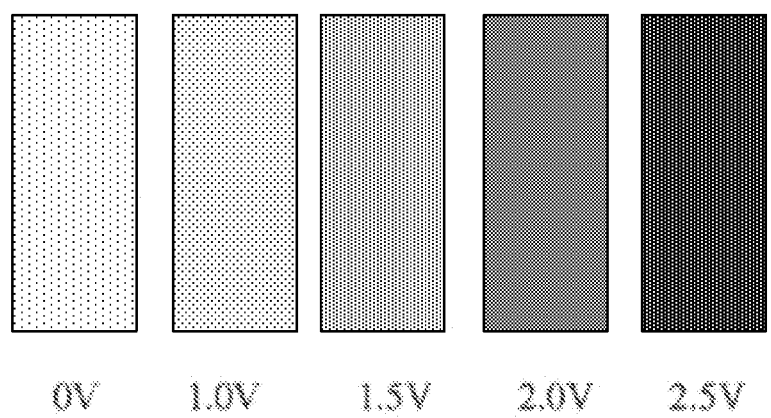
Figure 14A:
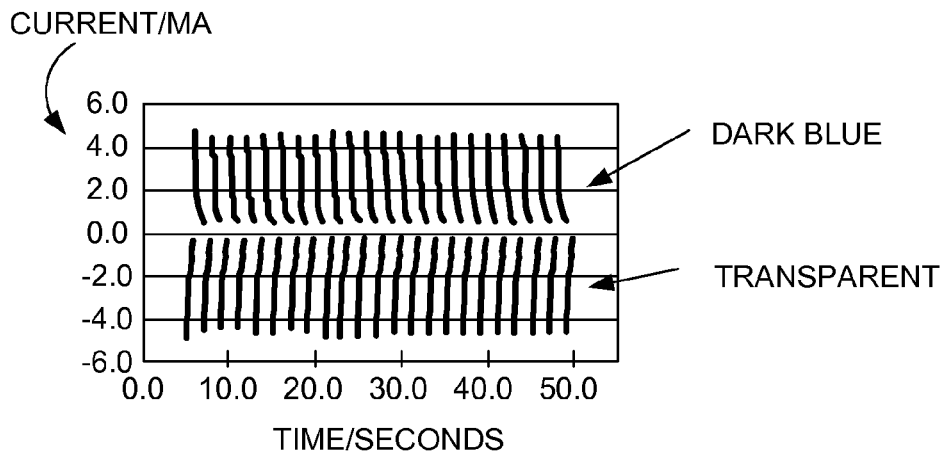
Figure 14B:
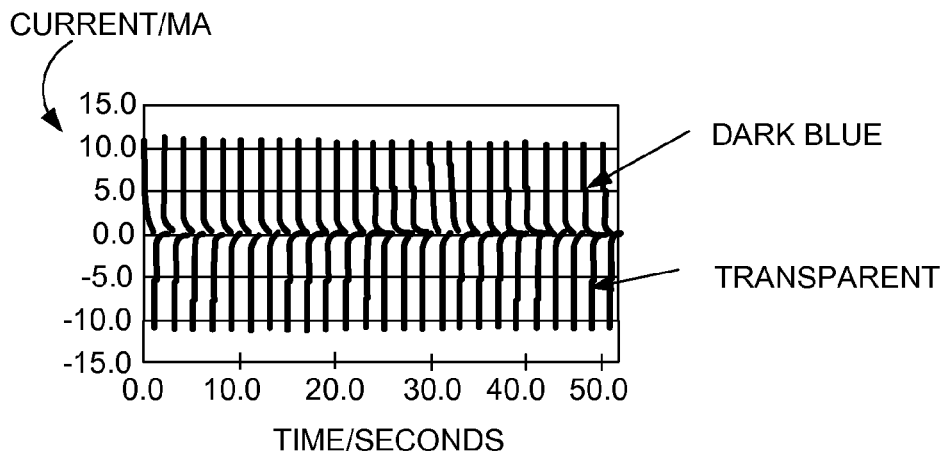
Figure 15:
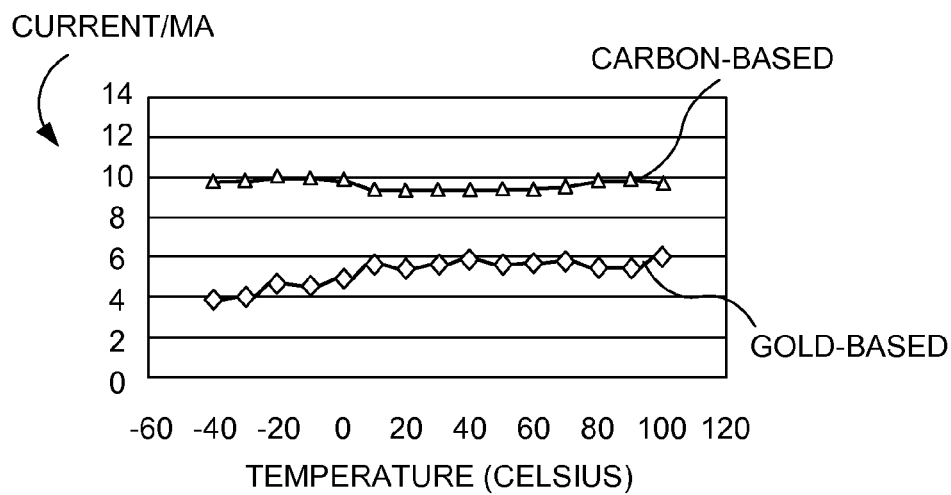
Figure 16A:
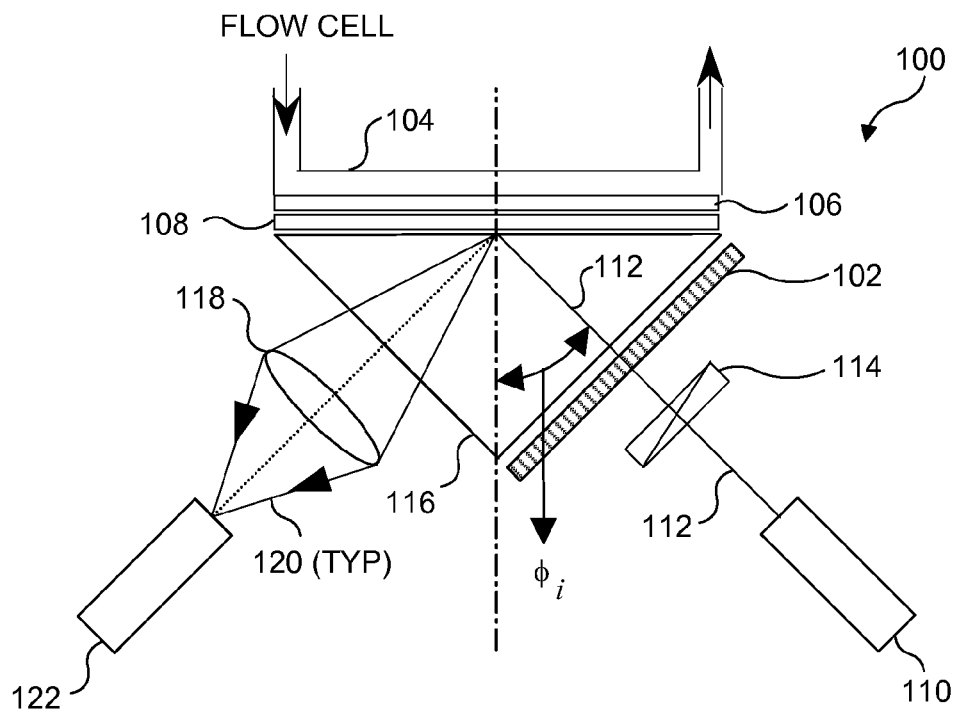
Figure 16B:
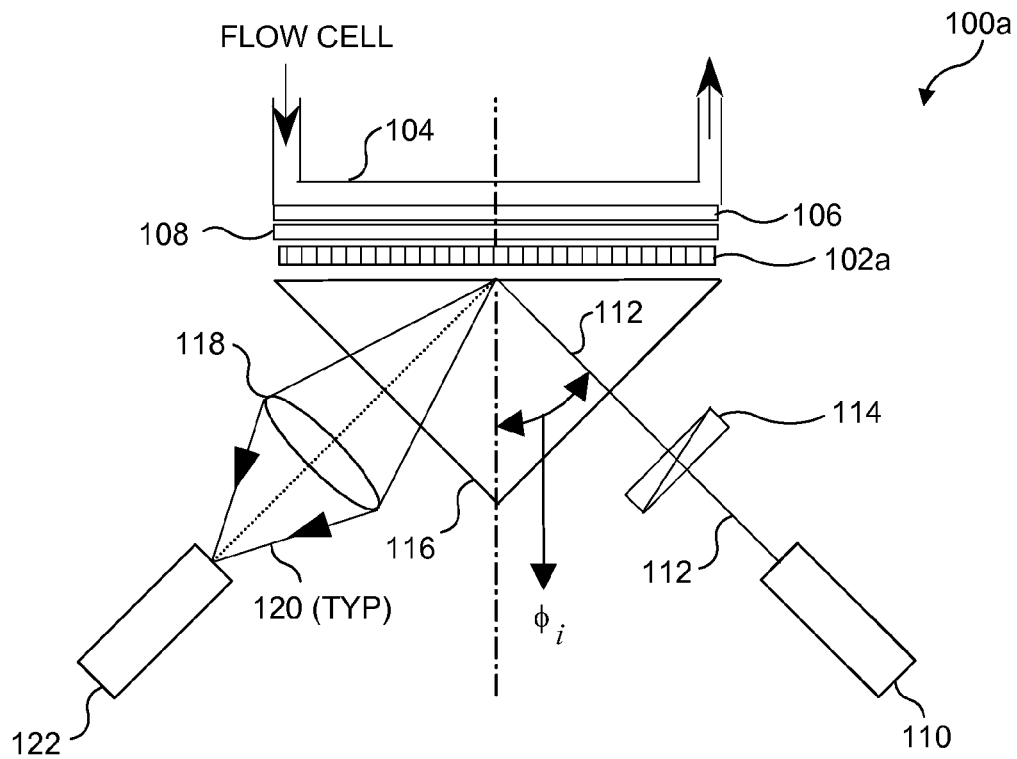
Figure 17:
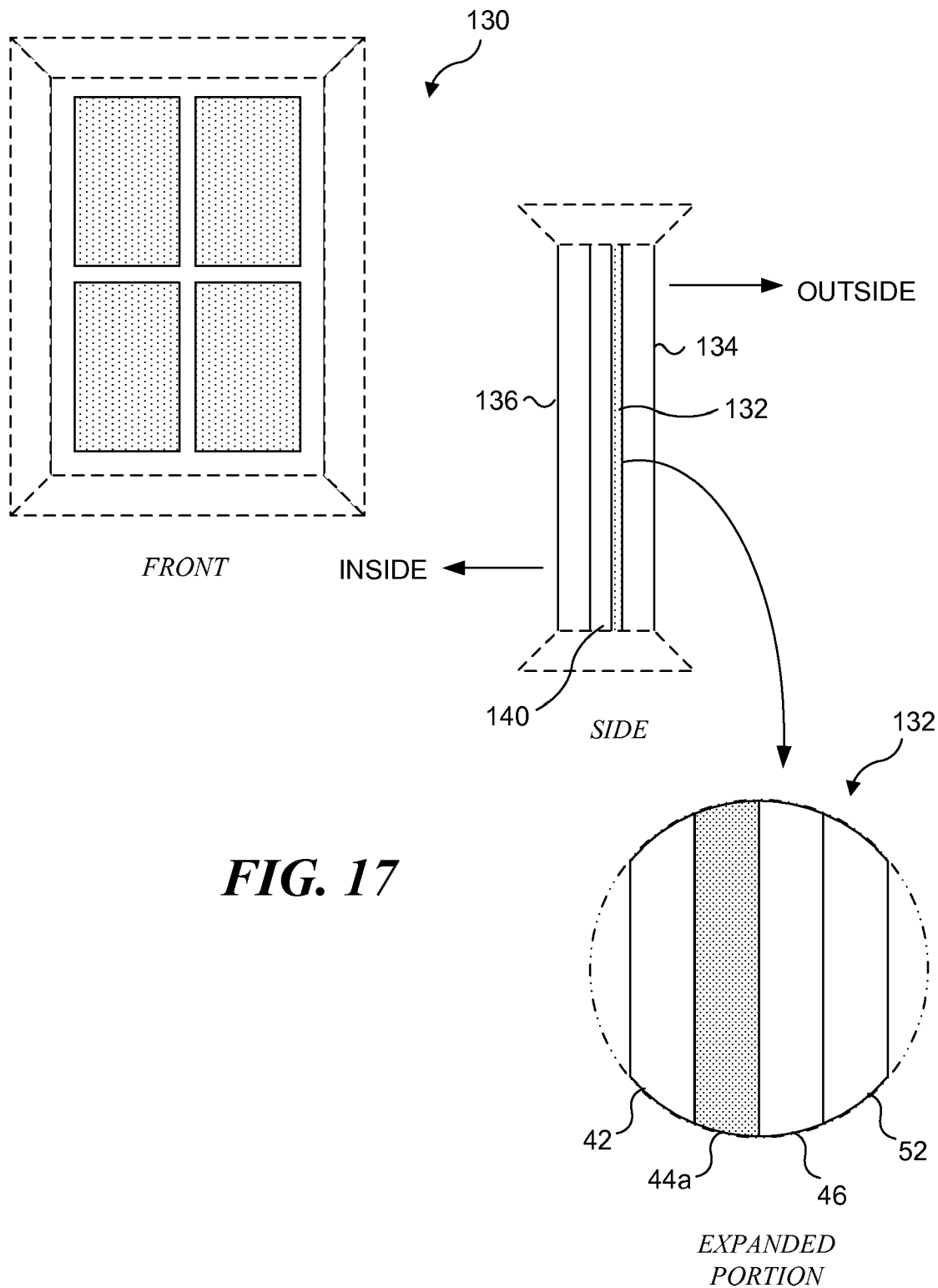
Figure 18:
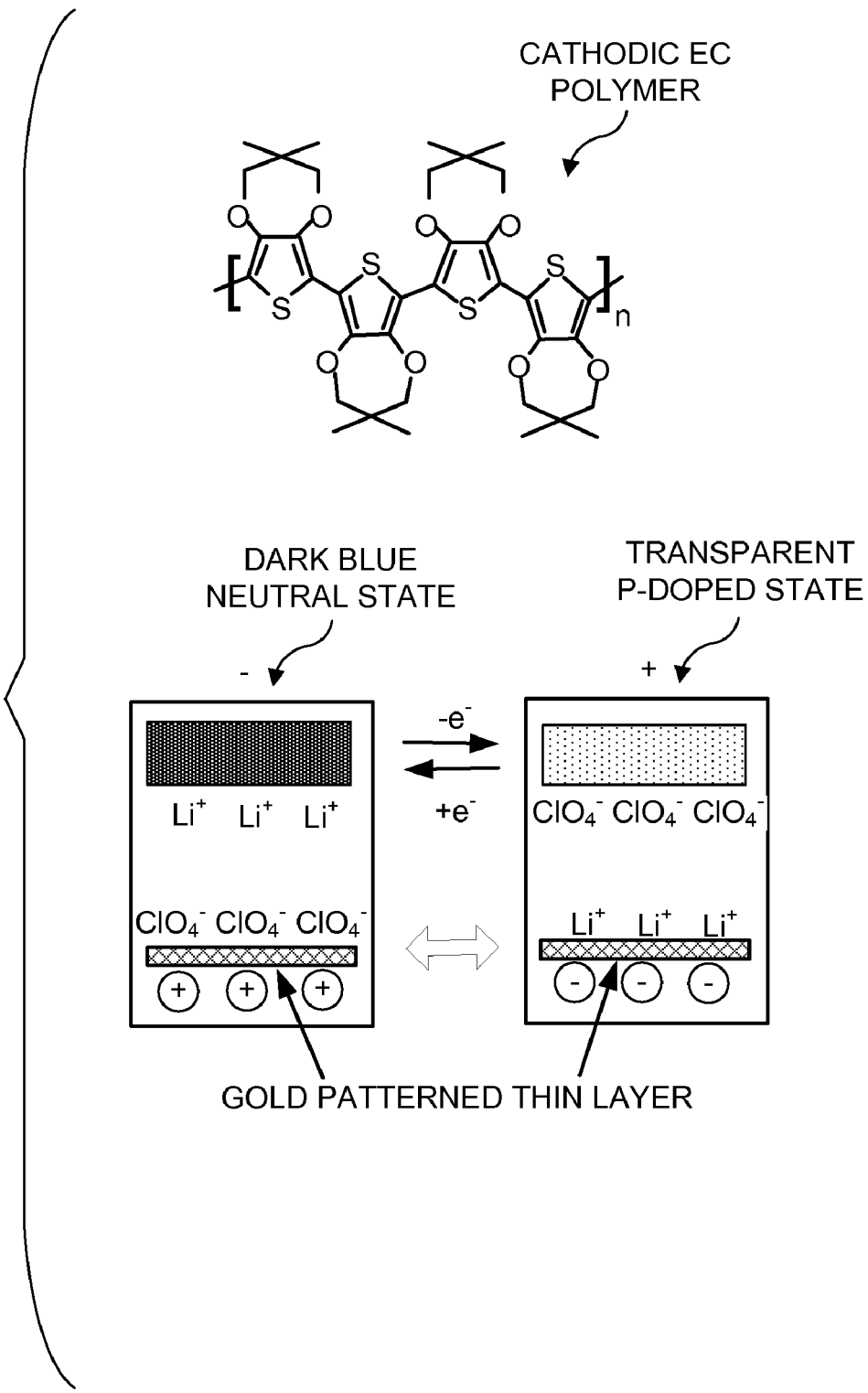
Figure 19A:
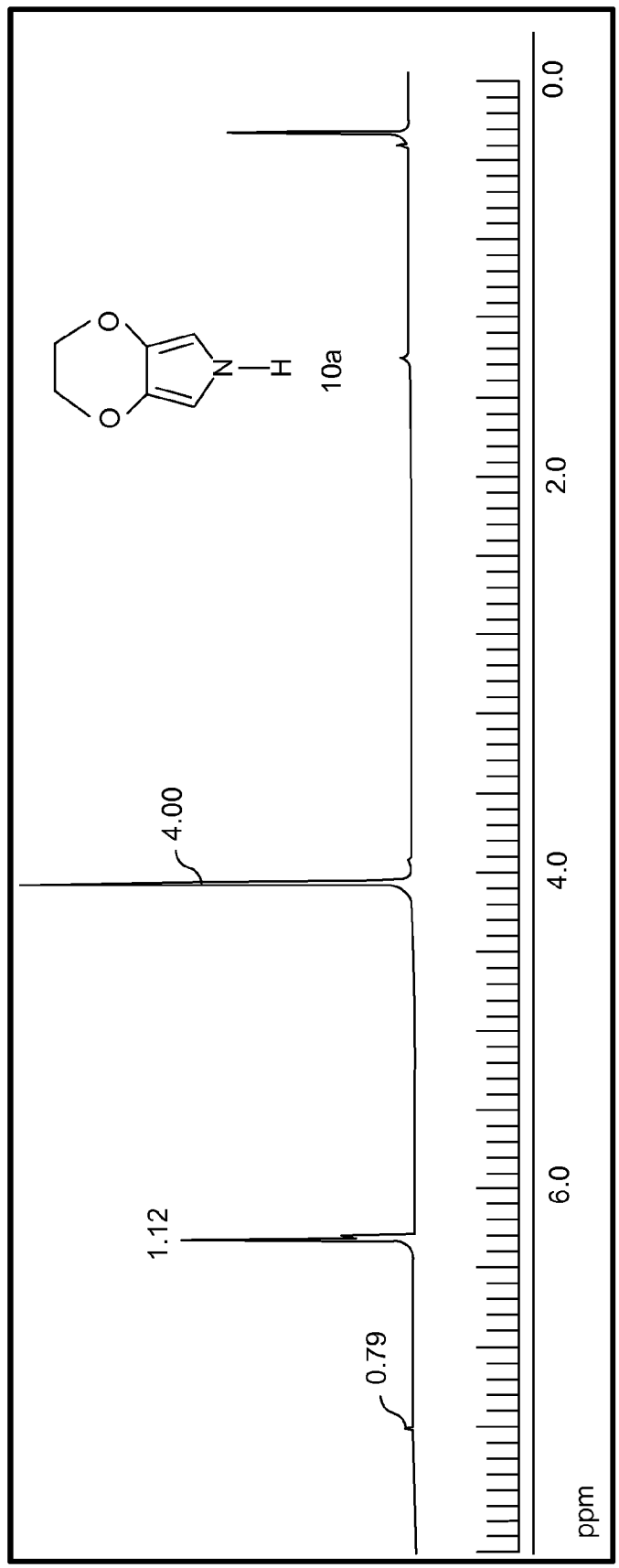
Figure 19B:
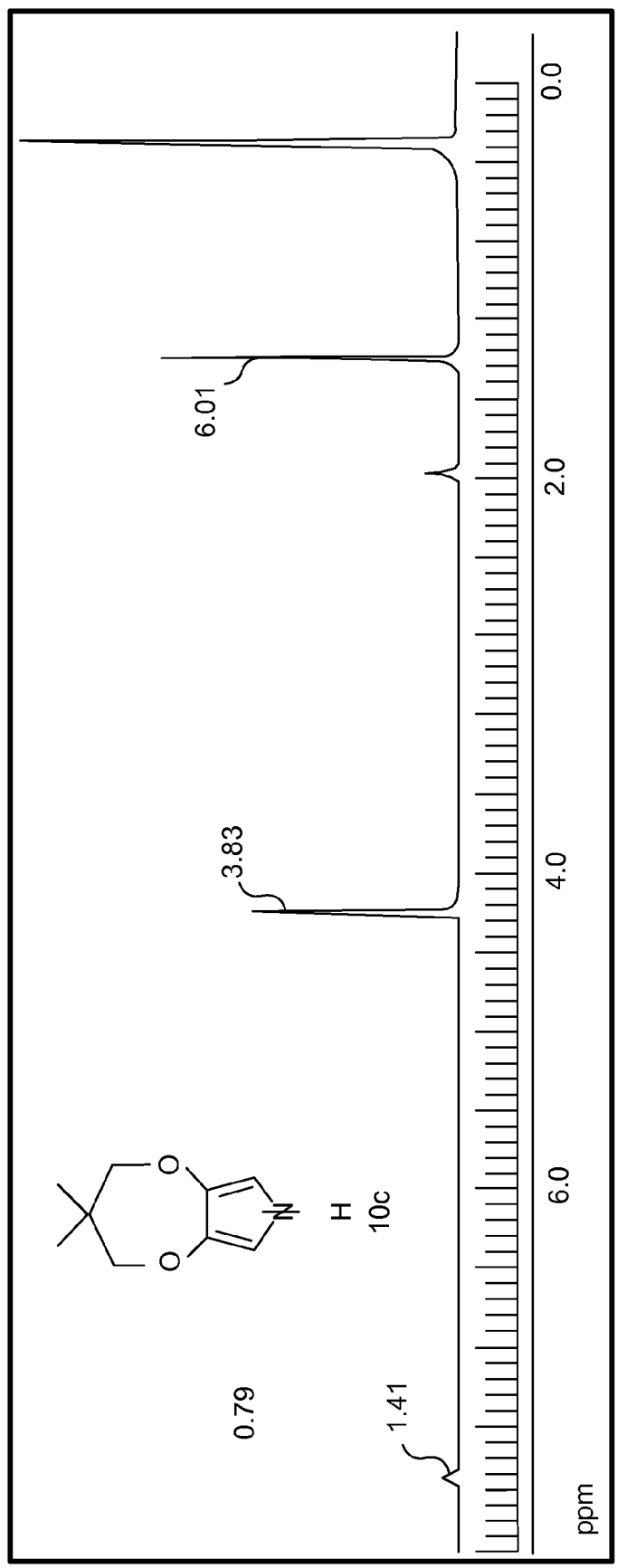
Figure 20:
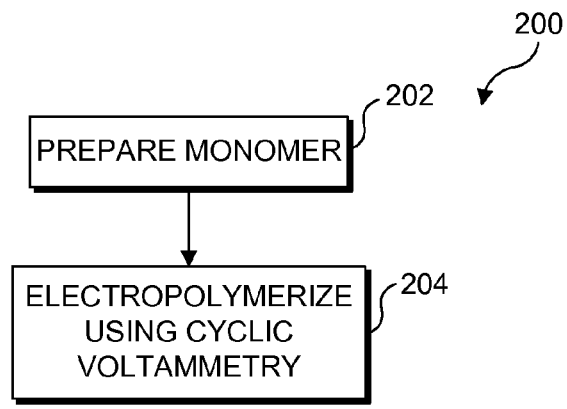
Figure 21:
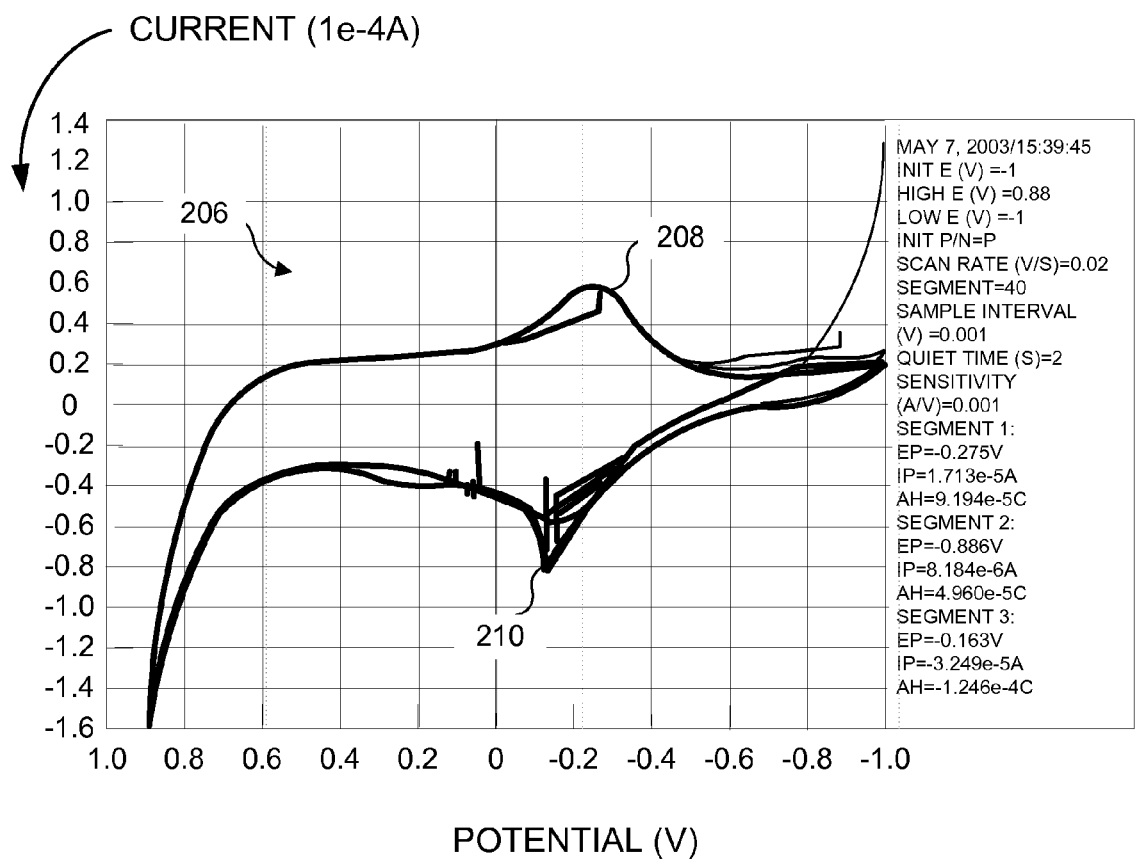
Figure 22:
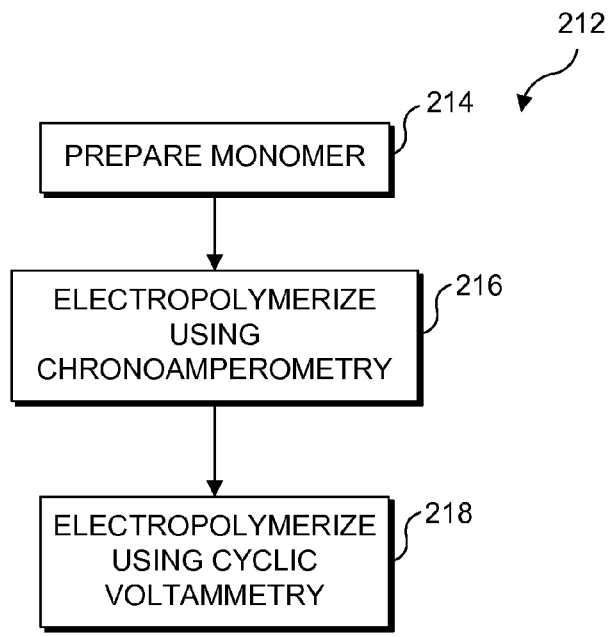
Figure 23:
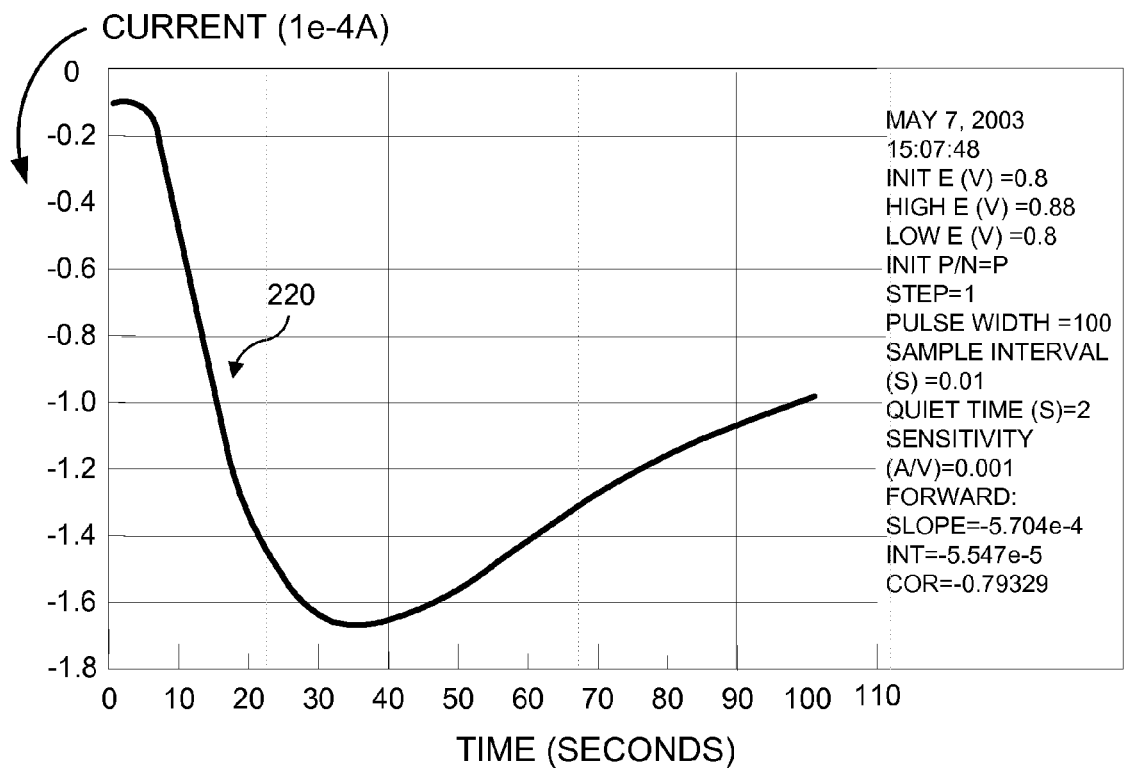
Figure 24:
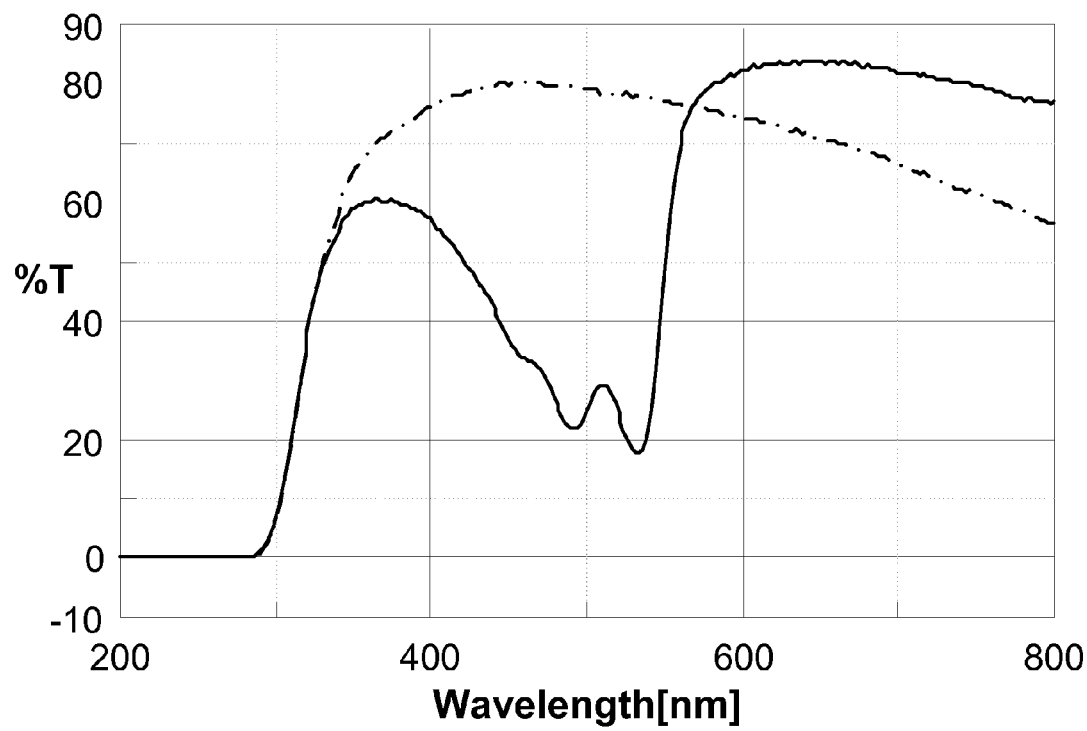
Figure 25:
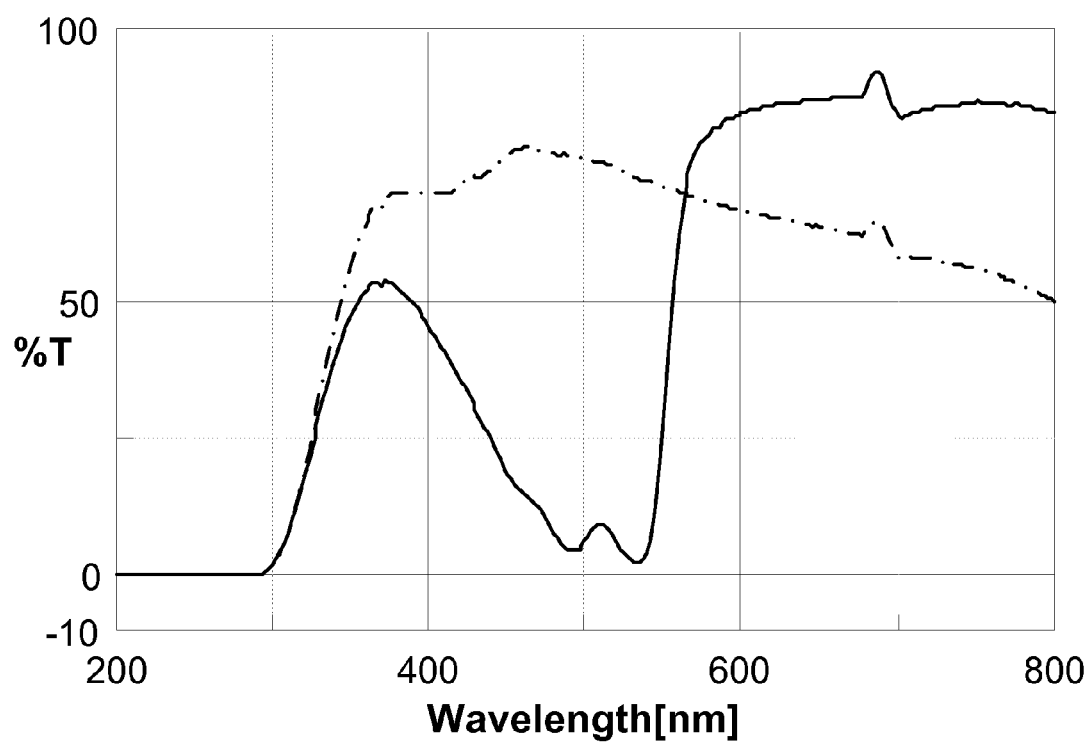
Figure 28A:
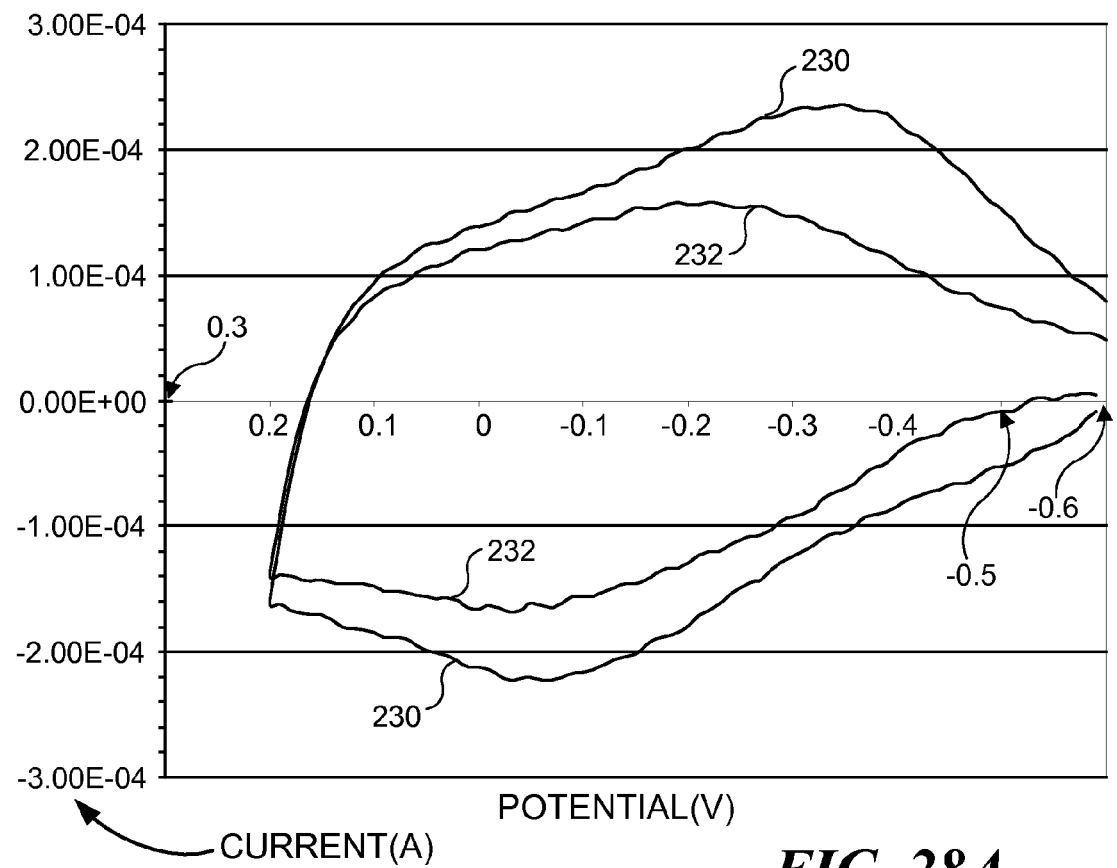
Figure 28B:
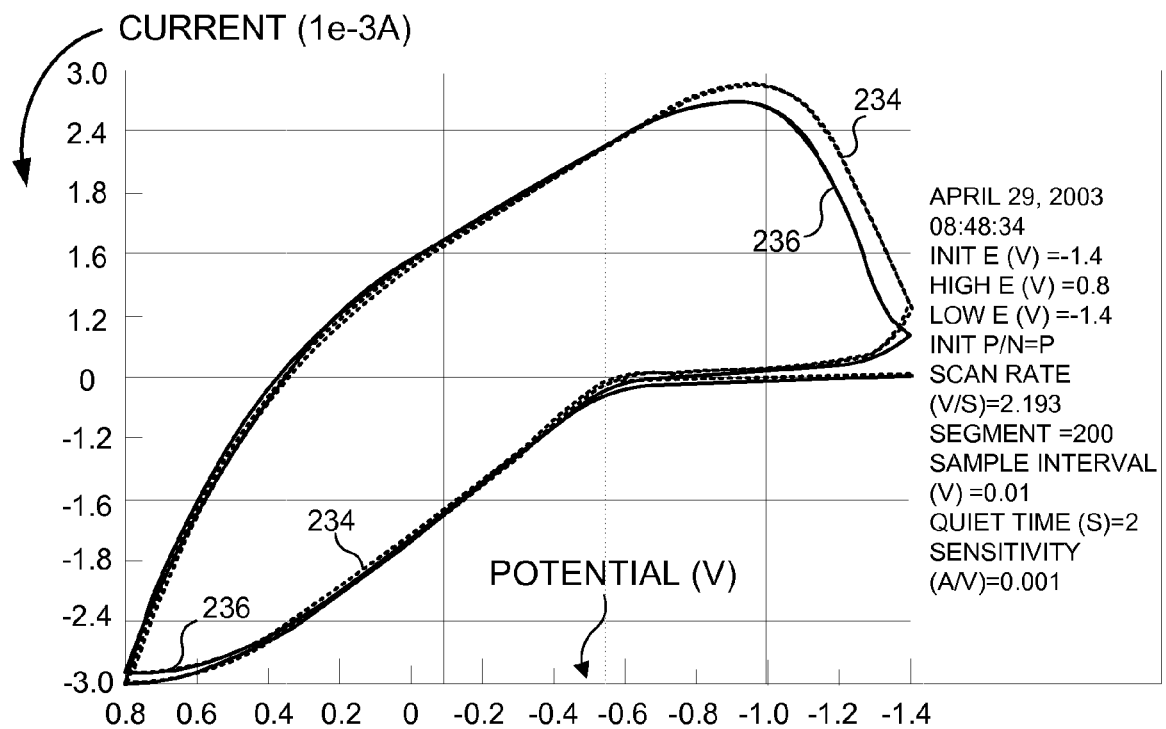
Figure 29:
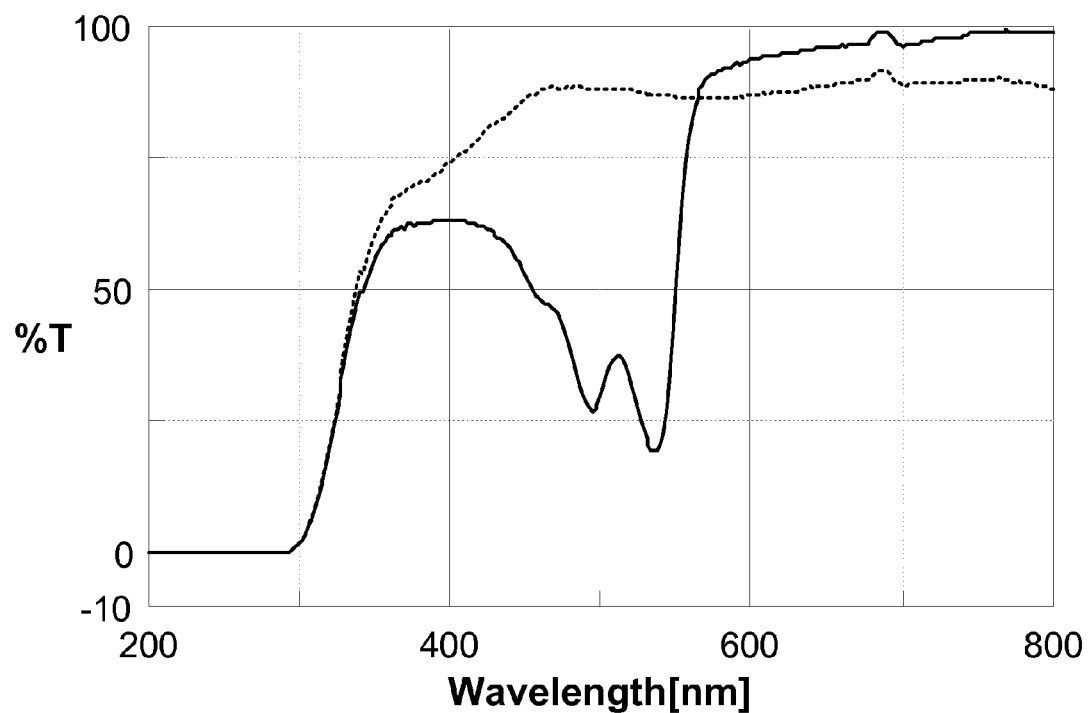
Figure 30:
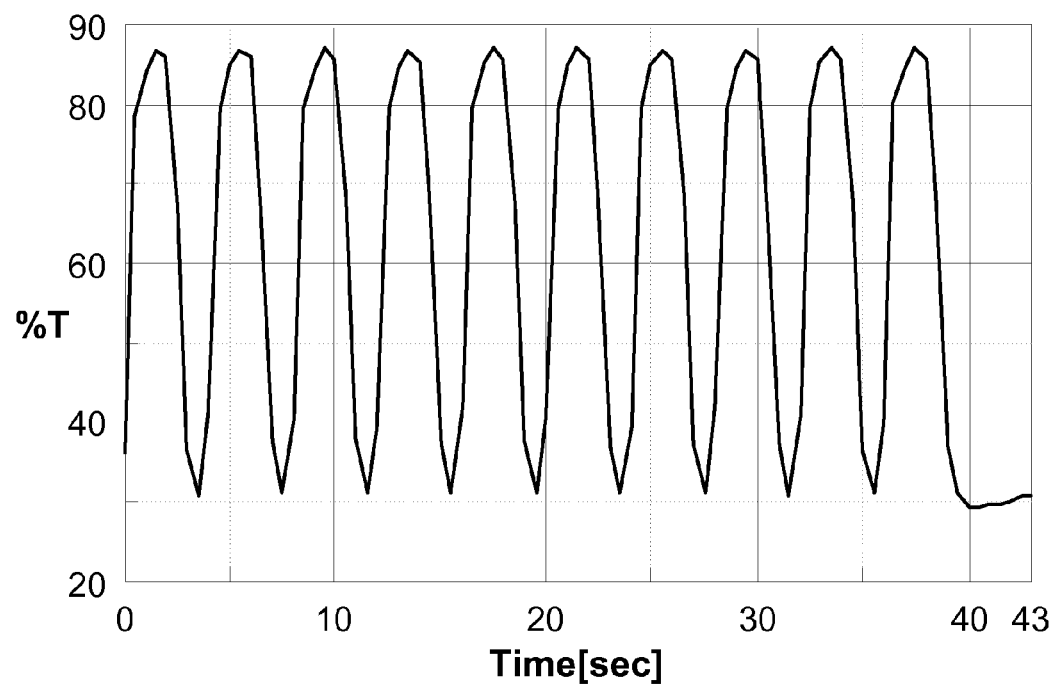

FIG. 2 schematically illustrates the synthesis of the monomer BEDOT-NMeCz, which may be beneficially employed as an anodic EC polymer once it has been polymerized;

FIGS. 3A and 3B are side elevational schematic illustrations of an EC device that includes a cathodic (PProDOT-Me$_2$) EC polymer film, an anodic (PBEDOT-NMeCz) EC polymer film, and a solid electrolyte layer;

FIGS. 4A and 4B are side elevational schematic illustrations of an EC device that includes a cathodic EC polymer film, a solid electrolyte layer and a counter-electrode;

FIG. 5A is a plan view of a gold-based counter-electrode being fashioned from a glass wafer;

FIG. 5B is a plan view of a gold-based counter-electrode;

FIG. 5C is a side elevational view of a gold-based counter-electrode;

FIGS. 6A and 6B illustrate alternative patterns that can be used to form a conductive layer on a counter-electrode;

FIG. 6C is a plan view of a graphite based counter-electrode;

FIG. 6D is a side elevational view of a graphite based counter-electrode;

FIG. 7A is a plan view of a web grid pattern based on concentric circles for use in depositing conductive materials on an optically transparent substrate to produce a counter-electrode;

FIG. 7B is a plan view of a web grid pattern based on concentric ellipses for use in depositing conductive materials on an optically transparent substrate to produce a counter-electrode;

FIG. 8A schematically illustrates a working model of a smart window including a PProDOT-Me$_2$ cathodic polymer film layer and a counter-electrode layer, to which either no voltage or a positive voltage is being applied, thus the smart window is in the oxidized or transparent state;

FIG. 8B schematically illustrates the working model of FIG. 8A, to which a negative voltage is being applied, thus the smart window is in the reduced or opaque state;

FIG. 9A graphically illustrates the repeatability of a color change in an EC device containing a PProDOT-Me$_2$ cathodic polymer film and a counter-electrode, in response to changes in applied voltage;

FIG. 9B graphically illustrates the repeatability of color changes in an EC device containing a PProDOT-Me$_2$ cathodic polymer film and a PBEDOT-NMeCz EC polymer film, in response to changes in applied voltage;

FIG. 10A graphically illustrates the transmittance of an EC device containing a PProDOT-Me$_2$ cathodic polymer film and a gold-based counter-electrode in the UV-visible spectrum;

FIG. 10B graphically illustrates the transmittance of an EC device containing a PProDOT-Me$_2$ cathodic polymer film and a graphite based counter-electrode in the UV-visible spectrum;

FIG. 11A graphically illustrates the optical switching abilities of an EC device containing a PProDOT-Me$_2$ cathodic polymer film and a gold-based counter-electrode, based on absorbance versus time;

FIG. 11B graphically illustrates the optical switching abilities of an EC device containing a PProDOT-Me$_2$ cathodic polymer film and a graphite-based counter-electrode, based on absorbance versus time;

FIG. 12 graphically illustrates that the time response of an EC device containing a PProDOT-Me$_2$ cathodic polymer film and a gold-based counter-electrode is substantially the same even at different potentials;

FIG. 13 graphically illustrates that the opacity of an EC device containing a PProDOT-Me$_2$ cathodic polymer film and a gold-based counter-electrode is a function of an applied potential;

FIG. 14A graphically illustrates the consistent repeatability of a current vs. time relationship for an EC device containing a PProDOT-Me$_2$ cathodic polymer film and a gold-based counter-electrode;

FIG. 14B graphically illustrates the consistent repeatability of a current vs. time relationship for an EC device containing a PProDOT-Me$_2$ cathodic polymer film and a graphite-based counter-electrode;

FIG. 15 graphically illustrates the temperature dependence of an EC device containing a PProDOT-Me$_2$ cathodic polymer film and a gold-based counter-electrode, and an EC device containing a PProDOT-Me$_2$ cathodic polymer film and a graphite-based counter-electrode, indicating that changes in temperature do not have a significant effect on the current within such devices;

FIG. 16A illustrates a first embodiment in which a DW is included in an SPR imaging system, for DNA chip reading;

FIG. 16B illustrates an embodiment in which a DW is included in an SPR imaging system, for DNA chip reading;

FIG. 17 is a schematic illustration of the EC devices of the present invention being integrated into a conventional dual pane architectural window;

FIG. 18 schematically illustrates the operation of a cathodic polymer EC layer paired to a counter-electrode layer;

FIG. 19A graphically illustrates the proton NMR spectra of a first monomer (propylenedioxypyrrole) suitable for preparing a red colored EC polymer film;

FIG. 19B graphically illustrates the proton NMR spectra of a second monomer (a dimethyl derivative to propylenedioxypyrrole) suitable for preparing a red colored EC polymer film;

FIG. 20 is a flowchart showing a sequence of logical steps executed in a first electropolymerization technique for producing EC polymer films from monomers in accord with the present invention;

FIG. 21 graphically illustrates a cyclic voltammetry polymerization curve for the electropolymerization of the monomer whose spectra is shown in FIG. 19B;

FIG. 22 is a flowchart illustrating a sequence of logical steps executed in a second electropolymerization technique for producing EC polymer films from monomers in accord with the present invention;

FIG. 23 graphically illustrates an exemplary chronoamperometry polymerization curve for the electropolymerization of the monomer whose spectra is shown in FIG. 19B;

FIG. 24 graphically illustrates a transmittance curve for an EC polymer film prepared using the first electropolymerization technique of FIG. 20;

FIG. 25 graphically illustrates a transmittance curve for an EC polymer film prepared using the second electropolymerization technique of FIG. 22;

FIG. 26A is a photograph of an EC polymer film, prepared using the second electropolymerization technique of FIG. 22, in the colored state;

FIG. 26B is a photograph of the EC polymer film of FIG. 26A in the bleached state;

FIG. 27A is a photograph of the EC polymer film of FIG. 26A in the colored state after 10,000 cycles;

FIG. 27B is a photograph of the EC polymer film of FIG. 26A in the bleached state after 10,000 cycles;

FIG. 28A graphically illustrates current vs. potential curves for fresh EC polymer films prepared using the first electropolymerization technique of FIG. 20 compared to the same films after 10,000 cycles;

FIG. 28B graphically illustrates current vs. potential curves for fresh EC polymer films prepared using the second electropolymerization technique of FIG. 22 compared to the same films after 10,000 cycles;

FIG. 29 graphically illustrates the transmittance of an EC polymer film prepared using the second electropolymerization technique of FIG. 22, after 10,000 cycles; and FIG. 30 graphically illustrates the transmittance change at a fixed wavelength of an EC polymer film prepared using the second electropolymerization technique of FIG. 22, after 10,000 cycles.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Overview of the Present Invention

The present invention is directed to methods for synthesizing EC polymer films having properties that can be beneficially employed in EC polymer devices, specific configurations of EC polymer based devices, and counter electrodes that can be beneficially employed in such EC polymer devices. More specifically, the present invention is directed to: (1) specific configurations for a grid of conductive material deposited onto a transparent substrate, the resulting grid and substrate being useful as a counter electrode in an EC polymer based device; (2) an imaging system including a digital window (DW); and, (3) a method for producing EC polymer films that can be beneficially incorporated in EC polymer devices.

Commonly owned U.S. Pat. No. 6,747,780, entitled "ELECTROCHROMIC ORGANIC POLYMER SYNTHESIS AND DEVICES UTILIZING ELECTROCHROMIC ORGANIC POLYMERS", describes counter electrodes useful for EC devices, an imaging system including a DW, and methods for making EC polymers. The concepts disclosed herein relate to the concepts described in U.S. Pat. No. 6,747,780, and the present application claims priority to U.S. Pat. No. 6,747,780. The following description includes both text of U.S. Pat. No. 6,747,780, as well as new text directed to the present invention.

New text relating to the first aspect of the present invention and specific configurations for a grid of conductive material deposited onto a transparent substrate can be found below in conjunction with the description of FIGS. 7A and 7B.

New text relating to an imaging system including a digital window can be found below in conjunction with the description of FIG. 16B.

Finally, new text relating to the method for producing red colored EC polymer films that can be beneficially incorporated in EC polymer devices can be found below in conjunction with the description of FIGS. 19A-30.

Synthesis of Blue EC Polymers

A first organic polymer expected to be useful in EC devices is poly[3,3-dimethyl-3,4-dihydro-2H-thieno[3,4-b][1,4]dioxepine], also known as dimethyl substituted poly(3,4-propylenedioxythiophene), or PProDOT-Me$_2$. FIG. 1A illustrates the preferred transetherification reaction 10 for the preparation of ProDOT-Me$_2$. A desired quantity of 3,4-dimethoxythiophene and 2,2-dimethyl-1,3-propanediol are dissolved in toluene and heated in the presence of p-toluenesulfonic acid monohydrate (at a concentration of 1.5 mol % of 3,4-dimethoxythiophene) for 10-20 hours at a temperature of 110° C. This process is referred to in the chemical arts as refluxing, as at a temperature of 110° C., toluene boils. In a refluxing process, a solution is boiled until a fraction of the solution (in this case the toluene fraction, as the 3,4-dimethoxythiophene, the 2,2-dimethyl-1,3-propanediol and the p-toluenesulfonic acid monohydrate fractions each have higher boiling points) is driven out of the solution as a vapor, and those vapors are then condensed and returned to the original solution.

The purpose of employing refluxing in the present invention is because methanol is produced as an undesirable byproduct when 3,4-dimethoxythiophene and 2,2-dimethyl-1,3-propanediol combine to form the desired product. Once some of the 3,4-dimethoxythiophene and 2,2-dimethyl-1,3-propanediol combine to form the desired product, the presence of the methanol byproduct actually inhibits further reaction between the 3,4-dimethoxythiophene and 2,2-dimethyl-1,3-propanediol. Thus to increase the amount of desired product that can be produced, the methanol byproduct is preferably removed as it is generated. Refluxing enables the methanol byproduct to be continually removed. Both methanol and toluene have boiling points that are lower than the boiling points of the other fractions; 3,4-dimethoxythiophene, 2,2-dimethyl-1,3-propanediol, p-toluenesulfonic acid monohydrate and the desired product. By heating the toluene to boiling, both the methanol and toluene are removed from the solution. The removed toluene and methanol are condensed and collected in a separate container. Calcium chloride is added to that separate container, which reacts with the methanol to enable the methanol to be removed from the toluene. The condensed toluene then is returned to the original solution (the boiling 3,4-dimethoxythiophene, 2,2-dimethyl-1,3-propanediol, p-toluenesulfonic acid monohydrate, toluene and the desired product). Thus a preferable step in the synthesis is removing the methanol using calcium chloride. As those of ordinary skill in the art will recognize, such a "salting out" process is sometimes employed in organic synthesis to remove undesirable reactants. In one embodiment, the condensed methanol and condensed toluene are filtered through solid calcium chloride. The resulting monomer, ProDOT-Me$_2$, is readily polymerized to PProDOT-Me$_2$. In the bleached state (when no voltage or a positive voltage is applied), PProDOT-Me$_2$ has a light blue tint, while in the opaque state (when a negative voltage is applied) PProDOT-Me$_2$ achieves a dark blue tint.

FIG. 1B schematically illustrates an apparatus 11 used to perform the above synthesis. The reactants (3,4-dimethoxythiophene, 2,2-dimethyl-1,3-propanediol, and p-toluenesulfonic acid monohydrate) are dissolved in toluene in a container 13. Sufficient heat is applied to container 13 (as noted above the boiling point of toluene is 110° C., and while the reagents added to the toluene will somewhat affect the boiling point of the solution, the boiling point of the solution will still be substantially 110° C.) so that the solution within the container gently boils. Toluene vapor (and any methanol byproduct) will be driven out of container 13 and into boiling tube 15. The vapors will rise into condenser 17, where the vapors cool and fall into packed calcium chloride 19. The movement of the vapors is indicated by a dashed line, while the movement of the condensed vapors is indicated by solid lines. The methanol is absorbed by the calcium chloride, and the condensed toluene rises to a level 21, where the condensed toluene returns back to container 13 via boiling tube 15. Preferably the amount of toluene employed, and the internal volume of apparatus 11 is such that some toluene always remains within container 13 (i.e. the solution never completely boils away) and that the condensed toluene is able to rise through the packed calcium chloride to level 21, such that some condensed toluene returns to container 13. Preferably a nitrogen blanket is introduced into apparatus 11, so that ambient oxygen does not introduce undesired byproducts or cross reactions.

A second organic polymer expected to be useful in EC devices is poly[3,6-bis(2-(3,4-ethylenedioxythiophene))-N-methylcarbazole, also known as PBEDOT-NMeCz. A preferred synthesis scheme 30 is shown in FIG. 2. First, (3,4-ethylenedioxythiophene) (EDOT) is treated with n-Butyl lithium in a solution of tetrahydrofuran (THF) at −78° C. for one hour. Those of ordinary skill in the art will recognize this step as that employed in the preparation of a Grignard reagent. The resulting Grignard reagent is then treated with magnesium bromide diethyl etherate. The product (i.e., the reagent B), remains in the THF solvent.

Then, a derivatized dibromocarbazole is combined with lithium hydride in dimethyl foramide (DMF) and kept at less than 10° C. for an hour. Methyl groups are slowly added at a 1:1 ratio, and the temperature is raised to 50° C. over a two hour period, yielding a methylated derivatized dibromocarbazole product (i.e., the reagent C), which is purified by washing with water and ether, and dried over sodium sulfate. Preferably methyl iodine (MeI) is used as a methylating agent. Reagents B and C are combined, resulting in the EDOT rings being affixed to the derivatized dibromocarbazole. The reaction between B and C is facilitated with a nickel catalyst, and requires that the reagents be held together at 50° C. over a twelve hour period, to yield BEDOT-NMeCz. The BEDOT- NMeCz monomer may then be polymerized to obtain the PBEDOT-NMeCz polymer to be used as an anodic layer in an ED device.

Synthesis of Red EC Polymers Films Using Electropolymerization

As described above PProDOT-Me$_2$ can be used in an EC device to enable a color change from light to dark blue. To achieve an EC device in which the color change is red, rather than blue, other EC polymers can be employed. One class of EC polymers in which the color change from bleached to opaque involve red, rather than blue, is based on 3,4-alkylenedioxypyrrole (XOP) and its derivatives. In particular, propylenedioxypyrrole (ProDOP) and its derivatives (for example, dimethlypropylenedioxypyrrole, or ProDOP-Me$_2$) are useful. Unfortunately, such EC polymers are challenging to produce as high quality films that are durable and provide a desirable contrast between bleached and unbleached states. FIG. 19A is a proton NMR spectra of ProDOP, and FIG. 19B is a proton NMR spectra of ProDOP-Me$_2$.

One aspect of the present invention is directed to a method for producing EC polymer films using electropolymerization. Such a method is particularly useful to generate high quality EC polymer films based on ProDOP and ProDOP-Me$_2$. The resulting EC polymer films have been shown to have a high contrast ratio of transmittance (>Δ70%) and to be very stable (exhibiting a repeatability of over 10,000 cycles). While the electropolymerization techniques described herein have been successfully employed to produce high quality EC polymer films based on ProDOP and ProDOP-Me$_2$, it should be understood that such electropolymerization techniques can be beneficially employed to polymerize other EC monomers, and the electropolymerization techniques of the present invention are not limited to use with ProDOP and ProDOP-Me$_2$ EC monomers.

Two related electropolymerization techniques were employed in polymerizing the ProDOP and ProDOP-Me$_2$ monomers in order to achieve a high quality EC polymer film. The goal was to produce a high quality dense EC polymer film. Density is required to achieve the high contrast between the bleached and unbleached states. High quality is required for repeatability over many cycles. EC polymer films that do not exhibit high contrast and repeatability over many cycles are not very useful as components in EC polymer based devices such as windows and displays.

EC polymer films were produced based on ProDOP and ProDOP-Me$_2$ using each of the two electropolymerization techniques, and the resultant EC polymer films were studied for contrast and stability.

A first electropolymerization technique is summarized in a flow chart 200 in FIG. 20. EC monomers are prepared in a block 202, and then cyclic voltammetry was employed, as indicated in a block 204, to polymerize the EC monomer and to deposit the resultant polymer as a film on a substrate, preferably an indium tin oxide (ITO) coated transparent substrate.

In an exemplary implementation of the electropolymerization techniques described herein, conventional methods for the preparation of ProDOP and ProDOP-Me$_2$ monomers were employed. Useful techniques for the preparation of these monomers are described in the following publications: (1) C. Cheng, J. Gulia, S. Rokita, C. Burrows, J. of Mole. Cat. A: Chemical, 113, pp. 379-391, 1996; (2) A. Mertz, R. Schropp, E. Dotterl, Synthesis, 7, pp. 795-800, 1995; and (3) K. Zong, J. R. Reynolds, J. Org. Chem. 66, pp. 6873-6882, 2001. Any of the techniques described in these or other related publications can be used to prepare the monomers, as indicated in block 202 of FIG. 20.

Referring now to block 204 of FIG. 20, polymerization of the EC monomer (ProDOP in one embodiment, and ProDOP-Me$_2$ in another embodiment) was achieved using cyclic voltammetry under the following conditions. Oxidative electrochemical polymerization of the monomer was carried out using multiple scan cyclic voltammetry (a voltage range of +0.8 to ~-1.0 V, a scanning rate of 20 mV/s and 10 cycles for ProDOP-(CH$_3$)$_2$; additional cycles were required for ProDOP) in a solution of 0.01 M of the monomer and 0.1 M of tetrobutylammonium perchlorate (TBAP) in propylene carbonate (PC), with a platinum (Pt) wire as the counter electrode. Attempts to complete the electropolymerization using lithium perchlorate (LiClO$_4$) as salt did result in a functional EC polymer film. However, the quality of the EC polymer film achieved using TBAP was significantly better. It appears that the lithium perchlorate salt absorbs moisture more readily, and the presence of moisture during polymerization noticeably degrades the quality of the resultant film.

FIG. 21 graphically shows an exemplary cyclic voltammetry polymerization curve 206 for the electropolymerization of ProDOP-(CH$_3$)$_2$. The cyclic voltammetry curve for ProDOP (not separately shown) is very similar to the polymerization curve shown in FIG. 21, displaying similar oxidative peak 208 and reductive peak 210. A high quality dense red color film was achieved relatively quickly using cyclic voltammetry to electropolymerize ProDOP-(CH$_3$)$_2$. A significantly longer time (35 minutes) was required to achieve a similar quality film using cyclic voltammetry to electropolymerize ProDOP.

The second electropolymerization technique in accord with the present invention is summarized in a flow chart 212 in FIG. 22. EC monomers are prepared in a block 214 (as described above). The second electropolymerization technique was used to produce a first EC polymer film from using ProDOP as a starting monomer, and a second EC polymer film using ProDOP-(CH$_3$)$_2$ as a starting monomer. Once the starting monomer is obtained or prepared, the monomer is polymerized first using chronoamperometry, as indicated in a block 216, followed by cyclic voltammetry, as indicated in a block 218. As described in greater detail below, the second electropolymerization technique combining both chronoamperometry and cyclic voltammetry appears to achieve a higher quality, more durable EC polymer film.

Referring now to block 216 of FIG. 22, the first step in the two part electropolymerization of the EC monomer (ProDOP in one embodiment, and ProDOP-Me$_2$ in another embodiment) was achieved using chronoamperometry under the following conditions. Oxidative electrochemical polymerization of the monomer was initiated using chronoamperometry (100 sec, 0.88 V for ProDOP-(CH$_3$)$_2$) to deposit a very thin, very uniform layer of EC polymer onto an ITO coated glass substrate using a platinum wire as a counter electrode. Once again, the selected monomer was placed into a propylene carbonate solution with tetrobutylammonium perchlorate salt (0.01 M of the monomer and 0.1 M of tetrobutylammonium perchlorate).

In a block 218, multiple scan cyclic voltammetry is employed to deposit additional polymer onto the uniform layer deposited using chronoamperometry. As noted above, the parameters of +0.8 to ~-1.0 V, a scanning rate of 20 mV/s and 10 cycles can be employed to deposit polymerized ProDOP-(CH$_3$)$_2$, with additional cycles being required for the deposition of an acceptably dense layer of polymerized ProDOP.

FIG. 23 graphically shows an exemplary chronoamperometry polymerization curve 220 for the electropolymerization of ProDOP-$(CH_3)_2$. The chronoamperometry curve for ProDOP (not separately shown) is very similar to the polymerization curve shown in FIG. 23.

Once an EC polymer film based on each monomer (ProDOP-$(CH_3)_2$ and ProDOP) was prepared using each of the above described electropolymerization techniques (cyclic voltammetry alone and chronoamperometry combined with cyclic voltammetry), optical switching studies were performed on the resultant EC polymer films. FIG. 24 graphically shows the results of such studies for an EC polymer film based on ProDOP-$(CH_3)_2$ and prepared using cyclic voltammetry alone, while FIG. 25 graphically shows the results of such studies for an EC polymer film based on ProDOP-$(CH_3)_2$ and prepared using chronoamperometry combined with cyclic voltammetry. Each graph is of transmittance vs. light wave range. The data were collected using spectroelectrochemistry and a UV-vis spectrophotometer. For each EC polymer film, the UV-visible spectrum was collected with the EC polymer in its fully transparent and fully colored states. The $\Delta$ T for the EC polymer film achieved using cyclic voltammetry alone is about 60%, as indicated in FIG. 24, while the $\Delta$ T for the EC polymer film achieved using chronoamperometry combined with cyclic voltammetry is about 70%, as indicated in FIG. 25. Higher contrast ratios in the visible region were observed for the EC polymer film prepared using chronoamperometry combined with cyclic voltammetry. This result can be attributed to the high quality of the EC film obtained using the combined method. The first step using chronoamperometry uniformly deposits a thin layer of EC polymer film on the ITO glass. The thin layer itself is not very useful for an EC polymer device, as dense layers are required for the desired color density and increased lifetime (as measured in cycles). Using cyclic voltammetry enables a dense EC polymer film to be formed. The rates of change for the EC polymer films prepared using either method are similar: less than 1 second. However, the repeatability of EC polymer film obtained using the combined method is significantly better, as discussed in detail below. It is believed that this result is due to the fact that the combined method achieves a more homogeneous EC film.

FIG. 26A is a photograph of an EC polymer film based on ProDOP-$(CH_3)_2$ and prepared using chronoamperometry combined with cyclic voltammetry with the EC polymer in the colored state. FIG. 26B is a photograph of the same EC polymer in the bleached state. These photographs were obtained using a freshly prepared EC polymer film (i.e., an EC polymer film that has not yet experienced many cycles of change).

FIGS. 27A and 27B are photographs of the same EC polymer film (based on ProDOP-$(CH_3)_2$ and prepared using chronoamperometry combined with cyclic voltammetry) after 10,000 cycles. FIG. 27A shows the EC polymer in the colored state, and FIG. 27B is a photograph of the same EC polymer in the bleached state. While there is some noticeable degradation of the bleached state shown in FIG. 27B compared with FIG. 26B, the difference in contrast between the colored and bleached states after 10,000 cycles is more than sufficient for use in an EC polymer device. It should also be noted that the degradation in the bleached state is not so significant as to be likely to impair the function of an EC polymer device. The changes in contrast between colored and bleached states shown in these photographs (FIGS. 26A and 26B, 27A and 27B) were obtained by varying the polarity of an applied potential from 0.8 to ~−1.4V for about 1 second.

The degradation of EC polymer films prepared using each of the electropolymerization techniques described above (cyclic voltammetry alone and chronoamperometry combined with cyclic voltammetry) after cycling was analyzed using cyclic voltammetry to provide a quantitative analysis. Again, the study was based on 10,000 cycles of the EC polymer film based on ProDOP-$(CH_3)_2$ and prepared using both techniques. Each film was cycled 10,000 times in an electrochemical reaction cell. Each polymer film (deposited on an ITO glass slide) was immersed in a polycarbonate and tetrobutylammonium perchlorate electrolyte (under inert gas) with a Pt wire used as an inert counter electrode. Very stable repeatability of the color change was observed. FIG. 28A graphically illustrates the repeatability of the ProDOP-$(CH_3)_2$ based polymer film prepared using cyclic voltammetry alone, while FIG. 28B graphically illustrates the repeatability of the ProDOP-$(CH_3)_2$ based polymer film prepared using chronoamperometry and cyclic voltammetry.

In FIG. 28A, a current vs. potential curve 230 for the freshly prepared film is slightly different than a corresponding current vs. potential curve 232 after 10,000 cycles. While curve 230 and curve 232 are not identical, the variation after 10,000 cycles is likely to be sufficiently small to enable such an EC polymer film to be beneficially employed in an EC polymer device, such as those described in greater detail below.

Turning now to FIG. 28B, note that a current vs. potential curve 234 for the freshly prepared film is very similar to a current vs. potential curve 236 after 10,000 cycles. The similarity between curves 234 and curve 236 indicates very little degradation has occurred. While EC polymer films prepared using cyclic voltammetry alone (FIG. 28A) provide functional films, EC polymer films prepared using both chronoamperometry and cyclic voltammetry appear to be of higher quality and suffer less degradation over 10,000 cycles.

After 10,000 cycles, the transmittance in the fully oxidized and fully reduced states of the EC polymer film based on ProDOP-$(CH_3)_2$ and prepared using the combined technique was measured. As graphically indicated by the transmittance curve after 10,000 cycles in FIG. 29, a maximum $\Delta$ T of 67% still remained. The transmittance change at a fixed wavelength (540 nm) of the same EC polymer was also tested, and the results are graphically shown in FIG. 30. FIGS. 29 and 30 support the conclusion that the EC polymer film based on ProDOP-$(CH_3)_2$ and prepared using the combined technique exhibits a high repeatability.

EC Device Configurations

Another aspect of the present invention is directed at specific configurations of EC devices utilizing EC polymers. Each configuration disclosed herein is based on a laminated system, including at least one EC polymer, a solid or liquid electrolyte, and upper and lower layers of transparent electrodes.

A first configuration for an EC device is schematically illustrated in both a transparent state 40a in FIG. 3A, and a colored state 40b in FIG. 3B. Note that structurally, there is no difference in the EC device in either the transparent state or the colored state. When a voltage is applied to the EC device, the EC polymers of the cathode and anode layers undergo a color change. The first configuration, as collectively illustrated in FIGS. 3A and 3B, thus includes a cathodic (PProDOT-$Me_2$) EC polymer layer and an anodic (PBEDOT-NMeCz) EC polymer layer. It should be noted that the polarity of the applied voltage is important. If a positive voltage is applied, the EC polymers of the present invention will either stay in the bleached state (assuming there was no negative voltage applied immediately prior to applying the positive voltage), or transition from the opaque state to the bleached state (assuming there was a negative voltage applied immediately prior to applying the positive voltage). If a negative voltage is applied, the EC polymers of the present invention will either stay in the opaque state (assuming there already was a negative voltage being applied immediately prior to applying additional negative voltage), or transition from the bleached state to the opaque state (assuming there was either a positive voltage applied immediately prior to applying the negative voltage, or no voltage applied immediately prior to applying the negative voltage).

A top layer is a transparent electrode 42, preferably formed from an ITO coated transparent substrate. While an ITO film on a transparent substrate represents a preferred transparent electrode, it should be understood that other materials, such as tungsten oxide and doped zinc oxide films over transparent substrates, can be beneficially employed as a transparent electrode. It should also be understood that while glass certainly represents a preferred transparent substrate, that other transparent materials, such as plastics and polymers, can also be beneficially employed as a transparent substrate. Thus the use of the term glass substrate should be considered to be exemplary, rather than limiting the scope of the present invention. The next layer is a cathodic PProDOT-Me$_2$) EC polymer layer, which in FIG. 3A is shown as a transparent layer 44a, and in FIG. 3B is shown as a colored layer 44b. It should be understood that when no voltage (or a positive voltage) is applied, the PProDOT-Me$_2$ EC polymer layer is not completely colorless. Instead, a light blue tint can be discerned (hence the shading in transparent layer 44a of FIG. 3A). As a negative voltage is applied, the PProDOT-Me$_2$ EC polymer layer becomes progressively more opaque, until it reaches saturation (a dark blue tint, as indicated by the shading in colored layer 44b of FIG. 3B).

Following the cathode EC polymer layer is a solid/gel electrolyte layer 46. The solid/gel electrolyte layer is followed by anodic (PBEDOT-NMeCz) EC polymer layer, which is illustrated as being a transparent layer 48a in FIG. 3A, and a colored layer 48b in FIG. 3B. Note that even with no voltage applied (or a positive voltage is applied), PBEDOT-NMeCz is not colorless, and a definite yellowish tint is apparent (hence, the shading in transparent layer 48a of FIG. 3A). Again, as a negative voltage is applied, the PBEDOT-NMeCz EC polymer layer becomes progressively more opaque, until it reaches saturation (a moderate blue tint, as indicated by the shading in colored layer 48b of FIG. 3B). The PBEDOT-NMeCz EC polymer layer is followed by a bottom layer, which is an additional transparent electrode 42, also preferably formed from indium tin oxide (ITO) coated glass.

The first configuration (FIGS. 3A and 3B) provides a dual EC polymer device, in which the darkness (or opacity) of colored state is increased by using two EC polymers. However, the transmittance of the bleached state is decreased, primarily because the anodic polymer has a noticeable tint in the transparent (or bleached) state. The monomer (e.g., BEDOT-NMeCz) used to generate the anodic EC polymer (e.g., PBEDOT-NMeCz) is somewhat difficult to synthesize, although the present invention does encompass a method for its synthesis.

The cathodic layer, which is based on a poly(3,4-propylenedioxythiophene) derivative (PProDOT-Me$_2$), expresses an excellent light transmittance change of 78 percent between the bleached and unbleached states. PProDOT-Me$_2$ exhibits rapid switching, low oxidation potentials, and excellent stability at ambient and elevated temperature.

In an EC device, the electrolyte layer must be ionically conductive, but electrically insulating. Both poly(vinyl chloride) (PVC) based and polymethylmethacrylate (PMMA) based gel electrolytes containing lithium perchlorate (LiClO$_4$) can be employed for solid electrolyte layer 46. Preferably, solid electrolyte layer 48 is fabricated from PVC (or PMMA), propylene carbonate (PC), ethylene carbonate (EC) and LiClO$_4$. The PVC (or PMMA) electrolyte mixture is dissolved in tetrahydrofuran (THF). Either PVC or PMMA based gel electrolytes provide high conductivity (2 mS/cm) at room temperature.

In such a gel electrolyte, the solid polymer matrix of PVC and PMMA provides dimensional stability to the electrolyte, while the high permittivity of the solvents EC and PC enable extensive dissociation of the lithium salts. The low viscosity of EC and PC provides an ionic environment that facilitates high ionic mobility.

Another useful gel electrolyte can be prepared from 3% LiClO$_4$, 7% PMMA, 20% PC and 70% acetonitrile (ACN) (% by weight). A simple synthesis of such a gel is achieved by first dissolving the PMMA and LiClO$_4$ in ACN. PC was dried over 4 angstrom molecular sieves and then combined with the other ingredients. The complete mixture was stirred for 10-14 hours at room temperature. A high conductivity (2 mS/cm), high viscosity and transparent gel electrolyte was formed. As described above, the solid polymer matrix of PMMA provides dimensional stability to the electrolyte, while the high permittivity of the solvents PC and ACN enable extensive dissociation of the lithium salt. The low viscosity of PC provides an ionic environment that facilitates high ionic mobility.

While gel electrolytes are preferred because they facilitate the production of a solid state device (the solvent liquid is contained within the polymer matrix), liquid electrolytes can be used in an EC device. One such liquid electrolyte can be achieved using 0.1M Tetrabutylammonium perchlorate (TBAP) in ACN. It is contemplated that materials other than PVC and PMMA can be employed to provide a polymer matrix for a gel electrolyte, and that materials other than TBAP and LiClO$_4$ can be employed as ionic sources.

A second preferred configuration for an EC device is similarly schematically illustrated in both a transparent state 50a in FIG. 4A, and a colored state 50b in FIG. 4B. Again, from a structural standpoint, there is no difference in the EC device in either the transparent state or the colored state. The second configuration, as collectively illustrated in FIGS. 4A and 4B, includes a cathodic PProDOT-Me$_2$ EC polymer layer and a counter electrode layer, but no anodic PBEDOT-NMeCz EC polymer layer. As before, the polarity of the voltage applied is critical in determining how such devices will respond.

Again, the top layer is transparent electrode 42, again, preferably ITO. The next layer is a cathodic PProDOT-Me$_2$ EC polymer layer, which in FIG. 4A is shown as a transparent layer 44a, and in FIG. 4B is shown as a colored layer 44b. After the cathode EC polymer layer comes a solid/gel electrolyte layer 46. The solid electrolyte layer is followed by a counter-electrode layer 52. No bottom transparent electrode layer is required.

Counter-electrode layer 52 is preferably gold-based, platinum-based, or highly conductive carbon based, and replaces the anodic EC polymer and bottom ITO electrode utilized in the first configuration described above. A preferred highly conductive carbon is graphite. It should be understood that while graphite certainly represents a preferred highly conductive carbon, that other highly conductive carbon materials can also be beneficially employed as a conductive film to be coated onto a transparent substrate to produce a counterelectrode. Many types of conductive carbons are available from a variety of manufacturers, such as Tokai Carbon Co. of Tokyo, Japan; and LORESCO INTERNATIONAL, of Hattiesburg, Miss. Thus the use of the term graphite herein should be considered to be exemplary, rather than limiting the scope of the present invention. It is further contemplated that nickel can be beneficially employed as a conductive film on a transparent substrate to produce a counter-electrode. The use of a counter-electrode can improve the speed of the color change between states, as well as the high contrast ratio between the two states. The counter-electrode material should be chemically stable, provide high electrical conductivity, and should be easy to fashion into a patterned substrate. Gold, highly conductive carbons, and platinum have been identified as being electrically conductive materials that can be beneficially employed for making a counter-electrode. It is contemplated that graphite will be very useful because of its low cost, and gold, while much more expensive, can be used in very thin layers, thereby minimizing the cost of a gold-based counter-electrode. Platinum, while electrically conductive, is likely to be so expensive as to preclude its use. It is further contemplated that other conductive materials can be employed to produce the counter-electrode.

A gold-based counter-electrode was produced as described below, and is illustrated in FIGS. 5A-5C. Polished float glass, 0.7 mm thick (available from Delta Technologies, Limited), was used as a substrate. The glass was cut into a 4 inch diameter glass wafer 56. Lithography and sputtering techniques were used for forming a gold pattern 58 on the glass wafer. Optionally, before the gold coating was applied, a layer 60 of titanium-tungsten (TiW) was first sputtered onto the glass substrate. TiW layers have often been used as barrier layers and capping layers in semiconductor manufacturing. The TiW layer helps tightly bind the gold layer to the glass substrate. The pattern design, or pattern geometry, ultimately effects the EC device. The wider the lines of conductive material on the counter-electrode, and the larger open areas of the patterning are expected to provide higher conductivity, thus enhancing the speed of the color change of the EC polymer, at the cost of decreasing transmittance through the counter-electrode when no voltage (or a positive voltage) is applied. Note that for some applications, particularly windows, transmittance through the EC device is very important. If the maximum transmittance through the EC device (or through any part of the device, such as the counter-electrode) is reduced to an unacceptable level, then the device may not be suitable for use in an application such as a window. The checkerboard pattern shown in FIGS. 5A and 5B offers a pattern that, when sufficiently small, is substantially transparent. It is contemplated that as an alternative to the square orifices in the gold layer, circular orifices or diamond shaped orifices would be equally useful, as respectively shown in FIGS. 6A and 6B. Preferably, less than 25 percent of the glass substrate is covered with gold, in order to maintain high transmittance. It should be noted that transmittance is maximized when the total area of the layer of gold (or graphite) is minimized, while conductivity is maximized when the area of the layer of gold (or graphite) is maximized. If an EC device must have excellent transmittance, and a somewhat slower response time is acceptable, then the percentage of the counter-electrode surface area devoted to a gold or graphite layer can be decreased. On the other hand, if response time is more important than transmittance, then the percentage of the counter-electrode area devoted to a gold or graphite layer can be increased. It has been empirically determined that covering less than 25 percent of the glass substrate with the conductive material represents a good compromise for EC devices that exhibit both rapid response times and acceptable transparency.

As noted above, highly conductive carbon (such as graphite) based counter-electrodes can also be employed. A first embodiment of a highly conductive carbon based counter-electrode is shown in FIGS. 6C and 6D. Once again, a preferred substrate is a polished float glass cuvette plate, about 0.7 mm thick. An ITO coating 64 is applied on one side of the polished float glass cuvette plate, and a carbon coating 62 is then applied over the ITO coating. Preferably, the highly conductive carbon material is graphite (HITASOL GA.66M). The electrical conductivity of this highly conductive carbon material is known to be not less than $10^{-2}$ S/cm. Preferably, less than 25 percent of the glass substrate is covered with the carbon, in order to maintain high transmittance. While lithography and sputtering were employed for gold patterning on glass substrate as described above, screen printing was employed for forming a graphite pattern on a glass substrate for the highly conductive carbon-based counter-electrode. It is anticipated that because screen printing technology requires less expensive equipment than does lithography and sputtering techniques, that mass production of highly conductive carbon-based counter-electrodes may be less expensive than mass production of gold-based counter-electrodes.

Note that in this embodiment of a graphite based counter-electrode, the glass substrate is coated with indium tin oxide on one side to form a transparent insulating substrate for the counter-electrode. Because the electric conductivity of gold is much higher than that of graphite, gold can be directly deposited on the glass substrate without ITO glass, but it is preferable to deposit a graphite pattern onto an ITO layer. While less preferred, it should be noted that an acceptable graphite based counter-electrode can be fashioned without the ITO layer illustrated in FIG. 7B.

Preferably, each polymer layer within these laminated devices are on the order of 150 nanometers in thickness, each solid electrolyte layer is approximately 30 microns in thickness, and the gold patterned layer on the counter-electrode is on the order of 50-100 nanometers in thickness. A preferable range of thickness for a graphite layer in a counter-electrode is also 50-100 nanometers, more preferably 100 nanometers. A preferred thickness for an ITO film is from about 10 nanometers to about 200 nanometers, with more electrical conductivity being provided by a thicker layer. Thus electrical conductivity within an EC device can be manipulated by adjusting a thickness of the ITO layer, especially an ITO layer employed in a counter-electrode. A preferred thickness for a transparent substrate (such as glass or plastic) utilized in a transparent electrode (or counter-electrode) is about 0.5-1.0 millimeters, most preferably 0.7 millimeters.

FIG. 7A shows another grid pattern that can be used to produce a counter-electrode in accord with the present invention. A web type grid 71 based on concentric circles is deposited on an optically transparent substrate such as those described above (i.e., glass or plastic, but preferably a polished float glass cuvette plate).

FIG. 7B shows yet another grid pattern that can be used to produce a counter-electrode in accord with the present invention. A web type grid 73 is based on concentric ellipses. As described in greater detail above, useful conductors include gold and carbon. When gold is employed, a layer of TiW can be used to enhance the bond of the gold to the substrate. While denser grids than grids 71 and 73 can be employed, preferably less than 25 percent of the substrate surface is covered with such conductive grids.

A platinum wire has been successfully employed as a counter-electrode in an EC device generally corresponding to the second configuration as shown in FIGS. 4A and 4B. While EC devices having a configuration (i.e., a cathodic EC polymer, a solid electrolyte layer, and a non EC polymer counter-electrode) preferably employ PProDOT-Me$_2$ as the cathodic layer, it should be understood that other EC cathodic polymers can be beneficially employed. It should be understood that a single polymer EC device can be fashioned using a counter-electrode and an anodic EC polymer, as opposed to a counter-electrode and a cathodic EC polymer. A single polymer EC device fashioned using a counter-electrode and an anodic EC polymer would be less transparent (i.e. the anodic EC polymer layer would be in its darker state) with no voltage (or a positive voltage) applied, and as a negative voltage is applied to the EC device the anodic EC polymer layer would transition to its more transparent state. This is the opposite of a single polymer EC device fashioned using a counter-electrode and a cathodic EC polymer, which is more transparent without a voltage (or a positive voltage) being applied, and become more opaque as a negative voltage is applied.

A sample device based on the single polymer/counter-electrode EC device described above was constructed using rectangular layers substantially 7 mm×50 mm. An ITO coated 7 mm×50 mm glass slide was prepared for the transparent electrode, and a layer of PProDOT-Me$_2$ was deposited on the ITO coated surface. A glass wafer onto which a grid pattern of gold had been deposited was cut into 7 mm×50 mm plates. Similar 7 mm×50 mm plates of graphite deposited in a grid pattern were also prepared. A PMMA/LiClO$_4$ gel electrolyte was uniformly placed between the cathodic EC polymer deposited on the ITO slide and the counter-electrode to form a layered device. Two devices were prepared, one with a gold counter-electrode, and one with a graphite counter-electrode layer. The graphite based counter-electrode differs from the gold-based counter-electrode in that a layer of ITO was first placed on the glass substrate before the graphite was deposited, while no such layer was employed in the gold-based counter-electrode. A rubber sealant was employed, and the assembled devices were allowed to cure for about 20 hours. It is anticipated that additional curing time might be beneficial, and that 20-30 hours represents a preferred range of cure times. The sealant employed was a parafilm, a readily available, semi-transparent, flexible thermoplastic sealant. A schematic illustration of these working models is provided in FIGS. 8A and 8B. It should be noted that the working models are consistent with the second embodiment discussed above with respect to FIGS. 4A and 4B. As above, the schematic model is shown in both an oxidized state (no voltage or a positive voltage applied) and a reduced state (a negative voltage applied).

FIG. 8A schematically shows a cross-sectional view and a top plan view of a working model in an oxidized state (no voltage or positive voltage applied). The cross-sectional view clearly shows the top layer as being transparent electrode 42, which was prepared by coating a glass slide with ITO. Immediately adjacent to transparent electrode 42 is transparent layer 44a, a thin film of the cathodic PProDOT-Me$_2$ EC polymer coated onto the transparent electrode 42. The next layer includes a generally circular solid/gel electrolyte layer 46, which is surrounded by a sealant 53 to prevent any of the electrolyte from leaking. As discussed above, the solid electrolyte layer (and sealant) is followed by counter-electrode layer 52. Note that the shape of the solid electrolyte layer defines that area of the EC polymer layer that will change color. Portions of the EC polymer layer that are not in contact with the electrolyte layer will not undergo a change in color.

In the present example, the EC polymer layer coated the entire generally square-shaped transparent substrate, the sealant was applied as a generally circular mask (i.e. the sealant was applied over the entire surface of the EC polymer layer except for a generally circular portion where no sealant was applied) and the solid electrolyte layer was deposited within the generally circular portion defined by the sealant mask. A quite sharp demarcation between portions of the EC polymer immediately adjacent to the solid electrolyte layer (such portions transitioning from a light state to a dark state under an applied negative voltage) was achieved relative to portions of the EC polymer layer immediately adjacent to the sealant (i.e. not immediately adjacent to the solid electrolyte layer, such portions not transitioning from a light state to a dark state under an applied negative voltage). Very little bleed through occurred at the interface between the sealant and the solid electrolyte layer, enabling a sharply defined window (i.e. the portion of the EC polymer layer that transitioned from light to dark under an applied negative voltage) to be achieved. Of course, the sealant mask and electrolyte area can be combined in shapes other than the generally circular shape employed here. Whatever shape the sealant can be conformed into can be used to define a window corresponding to the inverse of that shape, by filling the inverse (i.e. the void) with the electrolyte. Note that no bottom transparent electrode layer is required. FIG. 8B shows the working model after a negative voltage has been applied, and the portion of the EC polymer layer in contact with electrolyte has changed color, while the balance of the EC polymer layer (i.e. the portion in contact with the sealant) has not. With respect to FIGS. 8A and 8B, as noted above, the polarity of the voltage applied determines how such devices will respond.

Experimental Results

Electrochemical empirical studies were carried out with working samples corresponding to the second configuration as illustrated in FIGS. 4A and 4B. PProDOT-Me$_2$ was employed as the cathodic EC polymer, and a platinum wire was employed as the counter-electrode. The studies were executed using an potentiostat/galvanostat electrochemical analyzer, CH 1605A, from CH Instruments, with silver (Ag/Ag$^+$) as the reference electrode, an ITO-coated one-glass slide as the working electrode, and a platinum (Pt) wire as the counter-electrode. The electrolyte employed (in this case, a liquid electrolyte) was 0.1N TBAP/ACN. Spectro-electrochemistry was carried out on a Varian Corp. UV-Vis-NIR spectrophotometer. FIGS. 9A and 9B graphically illustrate the fast and repeatable actuation of each of the EC devices described above. In particular, FIG. 9A provides switching data for an EC device with a PProDOT-Me$_2$ cathodic layer, an electrolyte layer, and a counter-electrode layer, while FIG. 9B provides switching data for an EC device with a PProDOT-Me$_2$ cathodic layer, an electrolyte layer, and a PBEDOT-NMeCz anodic layer.

For optical switching studies, devices based on a PProDOT-Me$_2$ cathodic layer, an electrolyte layer, and a gold counter-electrode layer, and a PProDOT-Me$_2$ cathodic layer, an electrolyte layer, and a graphite counter-electrode layer were used. Again, spectro-electrochemistry was carried out on an UV-vis spectrophotometer. High contrast ratios in visible regions were observed for a gold-based counter-electrode device, as is graphically indicated in FIG. 10A. The high contrast ratios are attributed to the high transmittance of Au-based counter-electrode and the cathodic EC polymer in the oxidized state.

The colored state of a graphite based counter-electrode device shown in FIG. 10B was somewhat darker than the gold-based counter-electrode device, but the bleached state of the graphite based counter-electrode device was also darker, due to the lower percentage transmittance through the graphite based counter-electrode layer.

Optical switching is an important characteristic of an EC device, and each device, based on gold and graphite counter-electrodes, were tested for switching. FIG. 11A graphically illustrates the results for the gold-based counter-electrode device, while FIG. 11B graphically illustrates the results for the graphite-based counter-electrode device, based on absorbance under a wavelength of 580 nm and an application of 2.0V. Each device exhibited good repeatability and a rapid change in absorbance. The percentage transmittance in the bleached state of the graphite based counter-electrode device was lower than the gold-based counter-electrode device, but the absorbance response to potential is more rapid in the graphite based counter-electrode device. This result is likely due to the fact that graphite, whose electric conductivity is lower than that of gold, was patterned on ITO for enhancement of the overall conductivity.

For each device, the colors reached equilibrium within almost the same time (less than 1 second), even at the different applied potentials, as is graphically indicated in FIG. 12, with respect to the gold-based counter-electrode device. Note that the color saturation (i.e. the degree of opacity) is dependent upon the magnitude of the potentials applied, as is graphically indicated in FIG. 13, with respect to the gold-based counter-electrode device. While FIGS. 12 and 13 only refer to the gold-based counter-electrode device, the graphite-based counter-electrode device behaved similarly.

It is believed that the redox reaction occurs just on the surface of EC polymer film, and that the doping reaction requires a very small amount of ions. This property of the EC devices was studied using a potentiostat/galvanostat electrochemical analyzer, CH 1605A, from CH Instruments. By connecting the counter-electrode and the reference electrode to the above analyzer with a gold (or graphite) patterned glass slide as a counter-electrode, electrochemical data of an EC polymer-deposited ITO glass slide as the working electrode were measured. FIG. 14A graphically illustrates the repeatability of performance during the oxidization and reduction reactions of the gold-based counter-electrode device, while FIG. 14B shows the same result for the graphite-based counter-electrode device, upon varying polarity of a constant potential (i.e., 2.0 volts). Each device exhibited very stable repeatability within 1 second, a rapid response time. Under the same potential, the magnitude of the current of the graphite-based counter-electrode device was twice that of the gold-based counter-electrode. This result is due to the high electric conductivity of the graphite-based counter-electrode, resulting in a color change response time that is shorter than that of the gold-based counter-electrode device. This fact is apparent in FIG. 11B, where the absorbance vs. time curve of the graphite-based counter-electrode device has a very steep slope.

Temperature dependence of the color change performance of EC materials is also an important factor in designing EC devices. The magnitude of electric current of EC devices under the application of constant voltage represents color change property of the devices. The devices (gold and graphite-based counter-electrodes) were analyzed in a Temperature & Humidity Chamber (PDL-3K, ESPEC). Current time curves were measured by a potentiostat/galvanostat electrochemical analyzer at a constant 2.0 volts under various temperatures in the chamber. FIG. 15 graphically illustrates a plot of the maximum electric current in each EC device as a function of temperature. Current of the gold-based counter-electrode device increased very slightly within a temperature range of −40 to 10° C., but it became stable in the high temperature range of 10-80° C., while the graphite-based counter-electrode device was more stable over the entire range. The maximum current change for either device was less than $2 \times 10^{-3}$ mA from −40 to 100° C.

The speed of the switching between transparent and colored states of both the gold-based counter-electrode device and the graphite-based counter-electrode device is rapid, occurring in the range of about 0.3-1.0 seconds. The graphite-based counter-electrode device using ITO in the counter-electrode can achieve a 0.3-0.8 second response time, upon an applied 2 volts potential, and is repeatable (10,000 times). That performance is faster than achieved in the gold-based counter-electrode device (which did not use ITO in the counter-electrode). The gold-based counter-electrode device achieved a higher percentage change in transmittance between the transparent and opaque states. The power consumption of the devices are modest, 2-2.5 volts times 10-20 mA. The temperature range under which the switching is stable is relatively wide, −40° C.~100° C. In addition, the weight of the devices are minimal. The gold-based counter-electrode device and the graphite-based counter-electrode device exhibit good perceived contrast, require a low switching voltage, and hence, are of special interest for use in dialed-tint windows, large area displays, antiglare car rear-view mirrors, and other applications where controllable color switching is useful.

Specific Applications

Yet another aspect of the present invention relates to specific applications for EC devices. In a first embodiment, an EC device including a PBEDOT-NMeCz anodic layer is employed as a display. Because PBEDOT-NMeCz has a yellowish tint in the oxidized state, and a blue tint in the reduced state, a multicolor display can be achieved. Such an EC device preferably includes a plurality of pixels, each pixel being defined by an individually addressable grid of a dual polymer EC device including a PBEDOT-NMeCz anodic layer. A voltage can be applied to each pixel individually, enabling a flat panel display to be achieved in which the color of each pixel is separately controlled.

Still another application specific embodiment is directed to a DW for DNA chip reading technology based on SPR imaging with high lateral resolution. SPR imaging is an accepted technology, which currently utilizes expensive custom photo masks. In this embodiment, a DW including a plurality of individually addressable pixels arranged in a grid format is employed in the place of the conventional photomask. The DW includes a plurality of individual pixels, each of which is a laminated EC such as the dual polymer and single polymer devices described above. A voltage can be applied to each pixel individually, enabling selective masking to be achieved, pixel by pixel. Thus a DW provides a switchable window, from transparent to non-transparent (dark blue) by varying electric potential polarity. The laminated EC devices described above are fabricated in a digital (pixel) array, whose size are typically 0.5-50 microns across.

The impact of the above described DW technology is expected to be multifold and immediately transferable to DNA array chip technology, particularly the technology for reading unknown DNA and unknown molecules (in vitro or in vivo) by using SPR. A first example of using a preferred embodiment of a DW in accord with the present invention is shown in FIG. 16A. In FIG. 16A, a DW/SPR imaging system 100 includes a conventional SPR imaging system in which DW 102 is inserted. Conventional elements of DW/SPR imaging system 100 include a flow cell 104, a patterned analytic layer 106, a gold or silver layer 108, a laser light source 110 for directing light to the analytic layer along a first path 112, a first optical element 114 disposed in first light path 112 (for polarizing the light from light source 110), a prism 116 disposed in first light path 112 and adjacent to the analytic layer, such that light traveling along first light path 112 passes through the prism. A second optical element 118 is disposed along a second light path 120, and a charge coupled device (CCD) detector 122 disposed in second light path 120 to receive light focused by second optical element 118. Not separately shown are a plurality of electrical conductors coupled to each pixel of the DW, such that a voltage can be individually applied to each pixel, and a power supply electrically coupled to the electrical conductors and the laser light source.

A second example of using a DW in an SPR imaging system is shown in FIG. 16B. A DW/SPR imaging system 100a includes a conventional SPR imaging system in which DW 102a is inserted. Note that system 100a of FIG. 16B is very similar to system 100 of FIG. 16A. The difference between the two systems is the location of the DW. In system 100 (FIG. 16A), DW 102 is disposed in between first optical element 114 and prism 116. In system 100a (FIG. 16B), DW 102a is disposed in between prism 116 and patterned analytic layer 106.

By combining a DW with a conventional SPR imaging system that has been used as a real time analyzer of unknown molecules, including DNAs and RNAs, a new SPR system with high spatial resolution is achieved. The high resolution DW/SPR system is expected to analyze unknown molecules and DNAs on a real-time basis at a faster speed rate than can be achieved by conventional SPR imaging systems, by scanning through one group of molecules to another by opening the corresponding several pixels in a digital window. The DW can be left in place, and reconfigured by activating different pixels. In contrast, a photomask would have to be removed and replaced with a different mask to achieve a different masking pattern.

Yet another aspect of the present invention is a smart window that can be used in structural and architectural applications, such as in cars, planes, and buildings. Such a smart window is able to change state from being substantially transparent in a first state, with no voltage (or a positive voltage) applied, to being substantially opaque in a second state, with a negative voltage applied. FIG. 17 illustrates single or dual polymer EC devices such as those described above being incorporated into a conventional dual pane window 130. Note that FIG. 17 includes a front view, a side view, and an expanded portion view, each of which is appropriately labeled. Smart windows differ from conventional windows in that the EC device 132 layered between conventional glass outer pane 134 and inner pane 136, enables wires (not separately shown) extending from the smart window to be coupled to a controllable voltage source, such that the smart window will transition from being generally transparent to being significantly less transparent. If a void or gap 140 separates the panes of conventional glass, preferably the EC device 132 is coupled to outer pane 134, rather than inner pane 136. A first embodiment of a smart window is based on a dual polymer EC device using a ProDOT-Me$_2$ cathodic polymer layer, a solid electrolyte layer, and a PBEDOT-NMeCz anodic polymer layer, as described above. A second embodiment of a smart window is based on a single polymer EC device, using a PProDOT-Me$_2$ cathodic polymer layer, a solid electrolyte layer, and a counter-electrode layer, substantially as described above.

Because the dual and single polymer EC devices described above exhibit good perceived contrast and require a low switching voltage, they are anticipated to be of special interest in other applications as well, such as large area displays, automatic mirrors, and other applications where color change in response to an applied voltage is desirable.

Overview of Paired PProDOT-Me$_2$ & Counter-Electrode Functionality

PProDOT-Me$_2$ can be used as a cathodically coloring polymer. PProDOT-Me$_2$ is dark blue in color in its fully reduced form, and a very transmissive light blue in its fully oxidized form. This cathodically coloring polymer changes from a light color to a highly colored state upon charge neutralization (i.e. reduction) of the p-doped form. The $\pi$-$\pi$* transition is depleted at the expense of transitions outside the visible region. Therefore, the dominant wavelength of the color is the same throughout the doping process. The EC process of an EC device utilizing a PProDOT-Me$_2$ cathodic layer, a gel electrolyte containing lithium perchlorate (LiClO$_4$), and a gold-based counter-electrode is illustrated in FIG. 18, where the gold layer plays the role of the second layer required in the paired layer process explained below.

The EC process requires paired layers, with the PProDOT-Me$_2$ layer acting as a first one of the paired layers, and the gold-based counter-electrode acting as a second one of the paired layers. In the left side of FIG. 18, a negative voltage has been applied and the PProDOT-Me$_2$ polymer is in its reduced, highly blue colored state. The gold-based counter-electrode layer is attracting the negatively charged perchlorate (ClO$_4$) ions. In the right side of FIG. 18, no voltage (or a positive voltage) is being applied and the PProDOT-Me$_2$ polymer is in its oxidized, p-doped light color state. The gold-based counter-electrode layer is attracting positively charged lithium (Li) ions.

The gel electrolyte separating the PProDOT-Me$_2$ polymer layer and the gold-based counter-electrode layer is ionically conductive but electronically insulating, so the lithium and perchlorate ions are mobile and free to move between the PProDOT-Me$_2$ polymer side and the gold-based counter-electrode side under polarity change of applied potential.

The graphite-based counter-electrode works by the same mechanism. This electric double layer results in no chemical reaction, and causes no structural change in the counter-electrode layer (gold or graphite). The electric double layer can store both negative and positive charges.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A counter-electrode useful in an electrochromic device including a cathodic polymer layer comprising:
   (a) a substantially transparent and substantially non-conductive substrate; and
   (b) a generally non-transparent conductive material deposited onto the substrate in a generally concentric web-shaped pattern, such that less than an entire upper surface of the substrate is coated with the conductive material, and the generally concentric web-shaped pattern does not reduce a transmittance of the transparent non-conductive substrate by substantially more than about 25 percent, the generally concentric web-shaped pattern comprising a plurality of concentric elements radiating from a central point, and a plurality of spoke-like elements radiating from the central point.

2. The counter-electrode of claim 1, wherein the concentric elements are based on circles.

3. The counter-electrode of claim 1, wherein the concentric elements are based on ellipses.

4. A laminated electrochromic device comprising:
 (a) a transparent electrode layer;
 (b) a cathodic polymer layer comprising a relatively thin base layer generated using chronoamperometry, and a relatively thicker upper layer generated using cyclic voltammetry;
 (c) an electrolyte layer comprising a solid electrolyte; and
 (d) a counter electrode layer.

5. The laminated electrochromic device of claim 4, wherein the cathodic polymer layer comprises poly[3,3-dimethyl-3,4-dihydro-2H-thieno[3,4-b]-[1,4]dioxepine].

6. The laminated electrochromic device of claim 4, wherein the counter-electrode comprises:
 (a) a substantially transparent and substantially non-conductive substrate; and
 (b) a conductive material deposited onto the substrate in a generally web-shaped pattern, such that the generally web-shaped pattern does not reduce a transmittance of the transparent non-conductive substrate by substantially more than 25 percent.

7. The laminated electrochromic device of claim 6, wherein the generally web-shaped grid pattern is based on at least one of concentric ellipses and concentric circles.

8. The laminated electrochromic device of claim 6, wherein the conductive material comprises gold, further comprising a titanium-tungsten (TiW) layer disposed between the transparent electrode layer and the gold.

9. A surface plasmon resonance imaging system, comprising:
 (a) a flow cell;
 (b) a patterned analytic layer;
 (c) a light source directing light to the analytic layer along a first path;
 (d) a first optical element in the first path that polarizes the light;
 (e) a prism disposed in the first light path between the first optical element and the analytic layer, such that light traveling along the first path passes through the prism;
 (f) a digital window disposed between the prism and the analytic layer configured for selectively controlling whether light from the light source traveling along the first path reaches the analytic layer, without affecting the transmission of light from the light source through the prism, the digital window including a plurality of individually addressable pixels arranged in a grid format, each pixel being switchable between a transparent state and a non-transparent state by applying a voltage thereto, each pixel comprising a laminated electrochromic structure having a cathodic electrochromic polymer layer;
 (g) a plurality of electrical conductors coupled to each pixel, such that a voltage can be individually selectively applied to each pixel;
 (h) a power supply electrically coupled to said electrical conductors and said light source;
 (i) a second optical element disposed along a second path, said second optical element focusing light traveling from said analytic layer and passing the light that is focused through said prism; and
 (j) a detector disposed in the second path, said detector receiving light focused by the second optical element.

10. The surface plasmon resonance imaging system of claim 9, wherein each laminated electrochromic structure includes:
 (a) a first layer comprising a transparent electrode;
 (b) a second layer comprising a cathodic polymer layer including a relatively thin base layer generated using chronoamperometry, and a relatively thicker upper layer generated using cyclic voltammetry;
 (c) a third layer comprising a solid electrolyte;
 (d) a fourth layer comprising an anodic polymer layer including a relatively thin base layer generated using chronoamperometry, and a relatively thicker upper layer generated using cyclic voltammetry; and
 (e) a fifth layer comprising a transparent electrode.

11. The surface plasmon resonance imaging system of claim 10, wherein the anodic polymer comprises poly[3,6-bis(2-(3,4ethylenedioxythiophene))-N-methylcarbazole].

12. The surface plasmon resonance imaging system of claim 10, wherein the cathodic polymer comprises poly[3,3-dimethyl-3,4-dihydro-2H-thieno[3,4-b][1,4]dioxepine].

13. The surface plasmon resonance imaging system of claim 9, wherein each laminated electrochromic structure includes:
 (a) a first layer comprising a transparent electrode;
 (b) a second layer comprising a cathodic polymer layer including a relatively thin base layer generated using chronoamperometry, and a relatively thicker upper layer generated using cyclic voltammetry;
 (c) a third layer comprising a solid electrolyte; and
 (d) a fourth layer comprising a counter-electrode.

14. The surface plasmon resonance imaging system of claim 13, wherein the cathodic polymer comprises poly[3,3-dimethyl-3,4-dihydro-2H-thieno[3,4-b][1,4]dioxepine].

15. The surface plasmon resonance imaging system of claim 13, wherein the counter-electrode comprises:
 (a) a transparent non-conductive substrate; and
 (b) a conductive material deposited on the non-conductive substrate in a substantially web-shaped pattern, configured such that the pattern does not reduce a transmittance of the transparent non-conductive substrate by more than about 25 percent.

16. The surface plasmon resonance imaging system of claim 15, wherein the generally web-shaped grid pattern includes at least one of concentric circles and concentric ellipses.

* * * * *